US011129770B2

(12) United States Patent
Learmonth et al.

(10) Patent No.: US 11,129,770 B2
(45) Date of Patent: Sep. 28, 2021

(54) MODULAR MEDICATION CASE FOR IMPROVED REGIMEN COMPLIANCE

(71) Applicant: QuantaEd, LLC, San Diego, CA (US)

(72) Inventors: Donald Murray Learmonth, San Diego, CA (US); Shi-Ze Liu, Taipei (TW); Mehran Mehregany, San Diego, CA (US); Oliver Ian Yates, Kent (GB); James Albert Walker, Freehold, NJ (US)

(73) Assignee: QuantaEd, LLC, San Diego, CA (US)

( * ) Notice: Subject to any disclaimer, the term of this patent is extended or adjusted under 35 U.S.C. 154(b) by 355 days.

(21) Appl. No.: 16/333,021

(22) PCT Filed: Feb. 22, 2018

(86) PCT No.: PCT/US2018/019289
§ 371 (c)(1),
(2) Date: Mar. 13, 2019

(87) PCT Pub. No.: WO2018/156810
PCT Pub. Date: Aug. 30, 2018

(65) Prior Publication Data
US 2019/0201286 A1 Jul. 4, 2019

Related U.S. Application Data

(60) Provisional application No. 62/462,204, filed on Feb. 22, 2017.

(51) Int. Cl.
*A61J 1/03* (2006.01)
*A61J 7/04* (2006.01)
*G16H 20/10* (2018.01)

(52) U.S. Cl.
CPC .............. *A61J 1/035* (2013.01); *A61J 7/0418* (2015.05); *A61J 7/0436* (2015.05); *A61J 7/0481* (2013.01);
(Continued)

(58) Field of Classification Search
CPC ........ A61J 1/035; A61J 7/0481; A61J 7/0418; A61J 7/0436; A61J 2200/30; A61J 2200/70; G16H 20/10
See application file for complete search history.

(56) References Cited

U.S. PATENT DOCUMENTS

D139,383 S 11/1944 Lampl
2,885,110 A 5/1959 Tregilgas
(Continued)

FOREIGN PATENT DOCUMENTS

AU 2009238236 A1 12/2009
CN 101802648 A 8/2010
(Continued)

OTHER PUBLICATIONS

Officer: Ioannis Kousouretas, "International Search Report and Written Opinion", PCT/US2016/055535, Completed Jan. 16, 2017.
(Continued)

*Primary Examiner* — Michael Collins
(74) *Attorney, Agent, or Firm* — Kaplan Breyer Schwarz, LLP

(57) ABSTRACT

A modular smart packaging case comprising reversibly attachable electronics and detection modules is disclosed. The detection module includes a sensor array for monitoring the state of a blister pack containing a plurality of product units. The electronics module contains the high-value electronics required to read the sensors of the array, process the sensor output, and enable communications to and from the case. The electronics module and detection module are operatively coupled via a universal interface that enables the same electronics module to operate with a plurality of detection modules of different configurations. In some embodiments, the electronics module operatively couples with multiple detection modules.

33 Claims, 15 Drawing Sheets

(52) U.S. Cl.
CPC ........ *A61J 2200/30* (2013.01); *A61J 2200/70* (2013.01); *G16H 20/10* (2018.01)

(56) References Cited

U.S. PATENT DOCUMENTS

| | | |
|---|---|---|
| 3,243,081 A | 3/1966 | Schmank |
| 3,854,625 A | 12/1974 | Kuebler |
| D253,722 S | 12/1979 | Allen |
| D257,584 S | 12/1980 | Finkel |
| D275,833 S | 10/1984 | Malpass |
| 4,616,316 A | 10/1986 | Hanpeter et al. |
| 4,617,557 A | 10/1986 | Gordon |
| 4,660,991 A * | 4/1987 | Simon .................. G04B 37/127 368/10 |
| D305,960 S | 2/1990 | Wolff |
| D307,421 S | 4/1990 | Tedham et al. |
| D311,774 S | 10/1990 | Lax |
| D324,819 S | 3/1992 | Eisenberg |
| D339,742 S | 9/1993 | Walchek et al. |
| 5,267,650 A | 12/1993 | Gilbilisco |
| D358,546 S | 5/1995 | Walchek et al. |
| D358,762 S | 5/1995 | Walchek et al. |
| 5,412,372 A | 5/1995 | Parkhurst et al. |
| D398,521 S | 9/1998 | Coe |
| D399,134 S | 10/1998 | Lidle, Jr. |
| 5,852,590 A | 12/1998 | De La Huerga |
| D411,445 S | 6/1999 | Anderson |
| D414,106 S | 9/1999 | Anderson |
| D453,354 S | 2/2002 | Ikenaga et al. |
| 6,411,567 B1 | 6/2002 | Niemiec et al. |
| D460,690 S | 7/2002 | Doerschlag |
| 6,839,304 B2 | 1/2005 | Niemiec et al. |
| D514,308 S | 2/2006 | Wahl et al. |
| D516,801 S | 3/2006 | Jones et al. |
| D518,178 S | 3/2006 | Christiansen |
| 7,028,723 B1 | 4/2006 | Alouani et al. |
| 7,081,807 B2 | 7/2006 | Lai |
| 7,113,101 B2 | 9/2006 | Petersen et al. |
| D541,039 S | 4/2007 | Stugelmeyer |
| 7,258,005 B2 | 8/2007 | Nyce |
| D553,738 S | 10/2007 | Simonson |
| D585,638 S | 2/2009 | Skedelius |
| 7,502,666 B2 * | 3/2009 | Siegel ................... G16H 20/13 700/244 |
| D593,316 S | 6/2009 | Ruwiel |
| D606,393 S | 12/2009 | Easterbrook et al. |
| 7,630,788 B1 | 12/2009 | Reese |
| D612,594 S | 3/2010 | Wade et al. |
| D622,499 S | 8/2010 | Sprada et al. |
| 7,821,404 B2 | 10/2010 | Walker et al. |
| 7,928,835 B1 | 4/2011 | Jovanov et al. |
| D640,920 S | 7/2011 | Giraud et al. |
| 8,025,149 B2 * | 9/2011 | Sterry ................... A61J 7/0436 206/534 |
| 8,120,492 B2 | 2/2012 | Scharfeld et al. |
| 8,152,020 B2 | 4/2012 | Flowers et al. |
| D660,428 S | 5/2012 | Hohl |
| D663,110 S | 7/2012 | Marwah et al. |
| D663,112 S | 7/2012 | Fulmer Mason |
| D665,571 S | 8/2012 | Tello |
| D673,360 S | 1/2013 | Denzinger |
| D679,086 S | 4/2013 | Liguori |
| D689,688 S | 9/2013 | Horn |
| D693,999 S | 11/2013 | Alexander |
| 8,583,281 B2 | 11/2013 | Bear et al. |
| D694,906 S | 12/2013 | Priebe et al. |
| 8,733,432 B2 | 5/2014 | Labrecque |
| D711,882 S | 8/2014 | Yeo |
| D716,868 S | 11/2014 | Jansen et al. |
| 8,878,654 B2 | 11/2014 | Cohen-Alloro et al. |
| D719,216 S | 12/2014 | Jansen et al. |
| 8,960,440 B1 * | 2/2015 | Kronberg ................ A61J 1/035 206/531 |
| 8,963,710 B2 | 2/2015 | Huang et al. |
| D727,903 S | 4/2015 | Madsen |
| 9,070,063 B2 | 6/2015 | Carrender |
| D736,404 S | 8/2015 | Priebe et al. |
| 9,233,051 B2 * | 1/2016 | Tufi ....................... A61J 7/0418 |
| 9,387,154 B2 | 7/2016 | Aggarwal et al. |
| D787,812 S | 5/2017 | Ganesan et al. |
| 9,717,654 B2 | 8/2017 | Dickie et al. |
| 9,717,655 B2 | 8/2017 | Nova et al. |
| 9,770,390 B2 | 9/2017 | Aggarawal et al. |
| 10,278,287 B2 * | 4/2019 | Wilson ................... H05K 1/118 |
| 2005/0162979 A1 * | 7/2005 | Ostergaard .............. A61J 1/035 368/10 |
| 2005/0252924 A1 | 11/2005 | Pieper et al. |
| 2009/0283438 A1 | 11/2009 | Bourque |
| 2010/0006441 A1 | 1/2010 | Renaud et al. |
| 2010/0094455 A1 * | 4/2010 | Dehlin .................. A61J 7/0436 700/232 |
| 2010/0147733 A1 | 6/2010 | Pabari et al. |
| 2011/0100862 A1 | 5/2011 | Turkington et al. |
| 2012/0024889 A1 | 2/2012 | Robertson et al. |
| 2012/0145573 A1 | 6/2012 | Scharfeld et al. |
| 2012/0330684 A1 | 12/2012 | Jacobs et al. |
| 2013/0085365 A1 | 4/2013 | Marashdeh et al. |
| 2013/0126379 A1 | 5/2013 | Medhal et al. |
| 2013/0285681 A1 * | 10/2013 | Wilson ................... A61J 1/035 324/693 |
| 2013/0319902 A1 | 12/2013 | Tufi |
| 2013/0330684 A1 | 12/2013 | Dillon et al. |
| 2014/0118010 A1 | 5/2014 | Fan et al. |
| 2014/0255899 A1 | 9/2014 | Poullain |
| 2015/0224026 A1 * | 8/2015 | Davidson ........... B65D 83/0463 206/528 |
| 2015/0286852 A1 | 10/2015 | Sengstaken, Jr. |
| 2016/0000657 A1 | 1/2016 | Dickie et al. |
| 2016/0103085 A1 | 4/2016 | Mehregany |
| 2016/0158109 A1 | 6/2016 | Nova et al. |
| 2017/0283151 A1 * | 10/2017 | Stormer ................. A61J 1/035 |
| 2017/0294105 A1 | 10/2017 | Mehregany et al. |
| 2018/0044060 A1 | 2/2018 | Leahy |
| 2018/0060657 A1 * | 3/2018 | Stuck ....................... G06K 9/78 |
| 2019/0107501 A1 | 4/2019 | Mehregany |
| 2019/0244510 A1 | 8/2019 | Mehregany |

FOREIGN PATENT DOCUMENTS

| | | |
|---|---|---|
| CN | 103235013 A | 8/2013 |
| CN | 104302555 A | 1/2015 |
| EP | 2067718 A1 | 6/2009 |
| GB | 2463054 A | 3/2010 |
| JP | 2013-529095 A | 7/2013 |
| JP | 2015-516823 A | 6/2015 |
| JP | 2015-520702 | 7/2015 |
| WO | 94/07184 A1 | 3/1994 |
| WO | 2009/116108 A1 | 9/2009 |
| WO | 2010/045227 A1 | 4/2010 |
| WO | 2013/126897 A1 | 8/2013 |
| WO | 2013/159198 | 10/2013 |
| WO | 2015/191159 A2 | 12/2015 |
| WO | 2018/156810 A1 | 8/2018 |

OTHER PUBLICATIONS

Ramani Duraiswami et al., "Efficient 2D and 3D electrical impedance tomography using dual reciprocity boundary element techniques", "Engineering Analysis with Boundary Elements", Abstract only, Sep. 21, 1998, Publisher:Elsevier B.V., 13-31, vol. 22, Iss 1, https://doi.org/10.1016/S0955-7997(98)00028-9.

Sarkar et al., "Efficient 2D and 3D electrical impedance tomography using dual reciprocity boundary element techniques", "Engineering Analysis with Boundary Elements", Jul. 1998, Publisher: Research Gate.

SMRxT Realtime Medication Adherence, 2012-2014, Publisher: SMRxT Inc.; http://smrxl.com/index.php.

The Most Accurate Smart Blister in the World, "med-ic Smart Label", 2011, Publisher: IMC Information Mediary Corp.

Todd O'Connor, "mTouch (TM) Projected Capacitive Touch Screen Sensing Theory of Operation", ISBN:978-1-60932-466-7, Pub-

(56) References Cited

OTHER PUBLICATIONS lisher: Microchip Technology Inc., vol. DS93064A, pp. 1-16, Jan. 5, 2010, US.
Yang et al., "A Health-IoT Platform Based on the Integration of Intelligent Packaging, Unobtrusive Bio-Sensor and Intelligent Medicine Box", "Transactions on Industrial Informatics", 2014, pp. 1-13, Publisher: IEEE; DOI: 10.1109/TII.2014.2307795.
Applicant Initiated Interview Summary received for U.S. Appl. No. 29/614,053, dated Oct. 2, 2018.
Examiner initiated interview summary (PTOL-413B) received for U.S. Appl. No. 29/614,055, dated Dec. 20, 2018, 1 page.
Final Rejection received for U.S. Appl. No. 29/614,053, dated Jan. 10, 2019, 5 pages.
Notice of Allowance and Fees Due (PTOL-85) received for U.S. Appl. No. 29/614,049, dated Jan. 10, 2019, 5 pages.
Notice of Allowance and Fees Due (PTOL-85) received for U.S. Appl. No. 29/614,053, dated Feb. 21, 2019, 5 pages.
Notice of Allowance and Fees Due (PTOL-85) received for U.S. Appl. No. 29/614,055, dated Dec. 20, 2018, 9 pages.
Advisory Action (PTOL-303) received for U.S. Appl. No. 14/879,874, dated Aug. 1, 2018, 3 pages.
Advisory Action received for U.S. Appl. No. 16/179,287, dated Oct. 10, 2019, 3 pages.
Applicant Initiated Interview Summary (PTOL-413) received for U.S. Appl. No. 14/879,874, dated Mar. 13, 2019, 3 pages.
Applicant Initiated Interview Summary received for U.S. Appl. No. 14/879,874, dated Jul. 5, 2018, 3 pages.
Applicant Initiated Interview Summary received for U.S. Appl. No. 16/179,287, dated Oct. 3, 2019, 3 pages.
Ariel Bogle, "Soon Your Medicine Bottle Could Remind You to Take Your Pills", "Future Tense—The Citizen's Guide to the Future", Aug. 19, 2013, Publisher: ASU | New America | Slate.
Authorized Officer Shane Thomas, International Search Report and Written Opinion issued in International Patent Application No. PCT/US18/55267 dated Dec. 11, 2018.
Authorized Officer: Melissa Koval, "International Preliminary Report on Patentability" dated Sep. 1, 2017 in PCT Application No. PCT/US16/55516.
Cielo Pill Holders. Link: https://www.cielopillholders.com/products/slim-single-chamber-pill-holder. Visited Dec. 4, 2018. Slim Single Chamber Pill Holder. (Year: 2018).
Communication about intention to grant a European patent dated Feb. 11, 2020 for EP Application No. 16791135.3.
Communication about intention to grant a European patent dated Jul. 13, 2020 for EP Application No. 17719957.7.
Communication about intention to grant a European patent dated May 9, 2019 for EP Application No. 16791136.1.
Decision to grant a European patent dated Jun. 12, 2020, 2 pages.
Decision to grant a European patent dated Nov. 7, 2019 for EP Application No. 16791136.
Decision to grant a European patent dated Nov. 26, 2020 for EP Application No. 17719957.7.
English Translation of Office Action issued in Japanese Patent Application No. 2018-538051 dated Nov. 25, 2019.
English Translation of Office Action issued in Japanese Patent Application No. 2018-552841 dated Mar. 1, 2021.
Examiner initiated interview summary (PTOL-413B) received for U.S. Appl. No. 14/879,874, dated Jun. 3, 2019, 2 pages.
Examiner initiated interview summary received for U.S. Appl. No. 16/179,287, dated Oct. 31, 2019, 1 pages.
Examiner initiated interview summary received for U.S. Appl. No. 16/290,656, dated Jul. 30, 2019, 1 page.
Examiner initiated interview summary received for U.S. Appl. No. 16/360,332, dated Apr. 14, 2020, 2 pages.
Office Action issued in counterpart Japanese patent application No. 2018-538051, dated Apr. 27, 2020, 6 pp.
Office Action issued in counterpart Japanese patent application No. 2018-538053, dated Mar. 2, 2020, 4 pp.
Office Action issued in counterpart Japanese patent application No. 2018-538053, dated Aug. 26, 2019, 11 pp.
Office Action issued in counterpart Chinese patent application No. 201780030375.4, dated Jul. 3, 2019, 14 pp.
Final Office Action received for U.S. Appl. No. 14/879,874, dated May 14, 2018, 35 pages.
Final Office Action received for U.S. Appl. No. 16/360,332, dated Feb. 5, 2020.
Final Rejection received for U.S. Appl. No. 16/179,287, dated Aug. 1, 2019, 11 pages.
International Search Report and Written Opinion issued in PCT Patent Application PCT/US2020/033820 dated Sep. 10, 2020.
Non-Final Office Action received for U.S. Appl. No. 14/879,874, dated Oct. 10, 2017, 29 pages.
Non-Final Office Action received for U.S. Appl. No. 15/170,121, dated Nov. 20, 2017, 17 pages.
Non-Final Office Action received for U.S. Appl. No. 15/223,779, dated Sep. 8, 2017, 13 pages.
Non-Final Office Action received for U.S. Appl. No. 16/360,332, dated Oct. 4, 2019, 32 pages.
Non-Final Rejection received for U.S. Appl. No. 14/879,874, dated Feb. 26, 2019, 40 pages.
Non-Final Rejection received for U.S. Appl. No. 16/100,430, dated Jan. 25, 2019, 7 pages.
Non-Final Rejection received for U.S. Appl. No. 16/179,287, dated Feb. 8, 2019, 9 Pages.
Non-Final Rejection received for U.S. Appl. No. 16/290,656, dated Jun. 28, 2019, 6 pages.
Notice of Allowance and Fees Due (PTOL-85) received for U.S. Appl. No. 14/879,874, dated Jun. 3, 2019, 19 pages.
Notice of Allowance and Fees Due (PTOL-85) received for U.S. Appl. No. 16/100,430, dated Mar. 13, 2019, 8 pages.
Notice of Allowance received for U.S. Appl. No. 15/223,779, dated Apr. 19, 2018, 8 pages.
Notice of Allowance received for U.S. Appl. No. 15/223,779, dated Aug. 9, 2018, 9 pages.
Notice of Allowance received for U.S. Appl. No. 16/156,603, dated Feb. 21, 2020.
Notice of Allowance received for U.S. Appl. No. 16/179,287, dated Oct. 31, 2019, 9 pages.
Notice of Allowance received for U.S. Appl. No. 16/290,656, dated Jul. 30, 2019, 9 pages.
Notice of Allowance received for U.S. Appl. No. 16/360,332, dated Apr. 14, 2020, 18 pages.
Notice of Allowance received for U.S. Appl. No. 16/385,176, dated Apr. 10, 2020, 6 pages.
Notice of Allowance received for U.S. Appl. No. 16/385,176, dated Mar. 17, 2020.
Office Action received for European Patent Application No. 16791135.3, dated Mar. 29, 2019, 4 pages.
Office Action received for European Patent Application No. 17719957.7, dated Aug. 5, 2019, 7 pages.
Officer: Jean Sommer, "International Search Report and Written Opinion", PCT/US2016/055516, Completed Jan. 5, 2017.
Authorized Officer: Gkama, Alexandra, International Search Report and Written Opinion issued in PCT patent application No. PCT/US2018/019289, dated May 16, 2018, 11 pp.

* cited by examiner

MODULAR MEDICATION CASE FOR IMPROVED REGIMEN COMPLIANCE

CROSS REFERENCE TO RELATED APPLICATIONS

This application claims the benefit of U.S. Provisional Patent Application Ser. No. 62/462,204, filed Feb. 22, 2017, entitled "Modular Medication Case for Improved Regimen Compliance," (Attorney Docket: 3005-006PR1), which is incorporated herein by reference.

If there are any contradictions or inconsistencies in language between this application and the case that has been incorporated by reference that might affect the interpretation of the claims in this case, the claims in this case should be interpreted to be consistent with the language in this case.

TECHNICAL FIELD

The present disclosure relates to packaging in general, and, more particularly, to smart packaging.

BACKGROUND

The term "packaging" refers to the collection of different components that surround a product from the time of its production until its use. It typically serves many purposes, often simultaneously, such as providing protection from physical damage during shipping and handling, theft deterrence, inhibiting contamination, providing protection from electrical damage due to electrostatic discharge, etc., preventing tampering, inhibiting product degradation, and the like.

In recent years, the blister card has become a primary form of packaging for many products, such as toys, hardware, electronics, and medications. The primary component of a blister card is a cavity made in a formable layer, which usually is made of a type of thermoformed plastic. In some cases, the formable layer is folded back onto itself, thereby sealing the cavity and forming a "clamshell" package. More typically, a lidding seal of metal foil is joined to the formable layer as a backing layer to seal the cavities thereby forming one or more enclosed reservoirs.

As the blister card has become rather ubiquitous, there has been increasing interest in improving its utility by adding intelligence. Referred to as "smart," "active," or "connected" packaging, such packages include sensors and monitoring circuitry that can be used to provide product status, monitor freshness, track temperature exposure, record shocks imparted to the package, send an alert when one or more product units have been removed from a package, and the like. Further, it is possible to include complex product codes that are very difficult to copy, thereby frustrating counterfeit attempts. As a result, such added intelligence can enhance theft deterrence, inhibit product counterfeiting, enable tracking of product end-to-end (i.e., from production to the consumer), etc.

Unfortunately, conventional approaches for providing intelligent packaging are typically complex, expensive, and often easily damaged. In addition, blister cards come in many forms and sizes, with the number of product sites varying over a wide range. As a result, conventional smart packaging approaches have had to be customized to the specific product being tracked. Such customized packaging is expensive, requires retooling for every new product introduction, and leads to inventory management issues, since it requires that each custom package have its own SKU (stock keeping unit). The costs associated with the development of customized electronics, packaging, as well as inventory control, tracking SKUs, etc., has, to date, limited the successful introduction of smart packaging in many applications.

The need for a simple, lower-cost smart-packaging approach that enables end-to-end tracking of a packaged product remains, as yet, unmet.

SUMMARY

The present disclosure describes embodiments of a smart medicine case without some of the costs and disadvantages of the prior art. Cases in accordance with the present disclosure are modular such that relatively more expensive components are located within an electronics module that is reversibly attachable with detection modules that contain relatively less expensive components. As a result, the electronics module can be re-used by detaching it from one detection module and re-attaching it to a different detection module. Embodiments in accordance with the present disclosure are particularly well suited for use in oral contraceptive pill (OCP) applications, long-term medication monitoring, and the like.

An illustrative embodiment is a modular medicine case that includes an electronics module and a detection module, where the modules are electrically and mechanically coupled via standard electrical and mechanical interfaces, respectively. A reversible latch engages automatically to join the two modules when they are brought into alignment via the mechanical interface.

The electronics module includes electrical componentry required for interfacing with a sensor array for monitoring the state of a blister card held in the detection module, as well as communications circuitry for wirelessly communicating with a base station. In the illustrative embodiment, the electronics module includes processing logic, memory, communications circuitry, power-conditioning electronics, and sensor-readout electronics. In some embodiments, additional electronics is included in the electronics module to facilitate, for example, detection of counterfeit blister cards, issue alerts to the user, accommodate multiple detection modules, interact with a smart stylus, and the like.

The detection module includes a printed-circuit-board comprising an array of capacitance sensors, a receiver for seating a blister card relative to the capacitance sensors, and a housing for enclosing the receiver and blister card. In some embodiments, the detection module includes one or more sensors other than capacitive sensors. In some embodiments, the detection module includes electronic circuitry configured, for example, to authenticate the blister card, interact with a smart stylus, and the like.

The electronics and detection modules are electrically coupled through an electrical interface, which is standardized such that the any of a plurality of detection modules can be electrically coupled with the electronics module.

In similar fashion, the modules are coupled through a mechanical interface that is standardized such that any of the plurality of detection modules can be mechanically coupled with the electronics module. The mechanical interface physically aligns the modules and the components of the electrical interface located on each module. In some embodiments, the mechanical interface is keyed to ensure proper orientation of the two modules when they are joined.

In the illustrative embodiment, the latch includes a pair of resilient catches that are disposed at the mating portions of the modules to rigidly hold the modules together when they are brought into their coupled relationship. In some embodiments, the latch comprises a different latching mechanism.

The modularity of embodiments in accordance with the present disclosure provides several advantages over the prior art, including:
 i. standard electrical and mechanical interfaces between the modules; or
 ii. robust mechanical interface and reliable electrical connectivity; or
 iii. consistent industrial design and quality; or
 iv. ease of detector-module interchangeability (i.e., no complicated assembly and disassembly); or
 v. amortization of the cost of expensive electronics over a plurality of detection modules; or
 vi. any combination of i, ii, iii, iv, and v.

In some embodiments, the modular medicine case includes expansion components that enable it to be stacked with other modular medicine cases to collectively define a multi-blister-card unit.

In some embodiments, a modular case includes a hinge that enables a single electronics module to electrically and mechanically couple with a plurality of detection modules, each containing a different blister card. In some of these embodiments, the hinging structure includes a track system that enables access to each detection module by allowing other detection modules to be rotated away from the desired detection module.

In some embodiments, a stylus is included in the modular case to facilitate dispensing of the tablets from the blister card. In some of these embodiments, the stylus is a smart stylus that includes one or more sensors (e.g., force sensors, contact switches, etc.), one or more photodiodes, magnets, motion sensors, and the like.

An embodiment in accordance with the present disclosure is a modular case for monitoring the state of a blister card that includes a forming film, a lidding film, and a first tablet contained in a first reservoir defined by the forming film and the lidding film, wherein the system comprises: (1) a first detection module comprising: (i) a first housing for holding the blister card; (ii) a receiver that is configured to locate the blister card in a first position within the first housing; and (iii) a first sensor that is configured to operatively couple with the blister card when the blister card is in the first position such that the first sensor is operative for providing a first electrical signal that is based on at least one of (a) the presence of the first tablet in the first reservoir and (b) the physical state of a first dispensing region of the lidding film; (2) a first electronics module comprising: (i) sensor circuitry that is operative for measuring the first electrical signal; (ii) communications circuitry configured to communicate with an external device; and (iii) a second housing for enclosing the sensor circuitry and the communications circuitry; and (3) a first electrical interface that is configured to reversibly electrically couple the first sensor and the sensor circuitry, wherein the first electrical interface includes a first socket and a first plug, and wherein the first electronics module comprises one of the first plug and the first socket, and wherein the first detection module comprises the other one of the first plug and the first socket.

Another embodiment in accordance with the present disclosure is a method for monitoring the state of at least one blister card, wherein the method comprises: (1) providing a first detection module comprising: (i) a first housing for holding a first blister card, wherein the first blister card includes a first forming film, a first lidding film, and a first plurality of tablets, each tablet of the first plurality thereof being held within a different first reservoir of a plurality thereof, the plurality of first reservoirs being arranged in a first arrangement, and each first reservoir of the plurality thereof including a first dispensing region; (ii) a first receiver that is configured to locate the first blister card in a first position within the first housing; and (iii) a first plurality of sensors that is arranged in the first arrangement, the first plurality of sensors being operative for providing a first plurality of electrical signals, each electrical signal of the first plurality thereof being based on at least one of (a) the presence of a different tablet of the first plurality thereof and (b) the state of a different first dispensing region of the plurality thereof; and (2) reversibly electrically coupling the first detection module and a first electronics module at a first electrical interface comprising a first socket and a first plug, wherein the first electronics module includes: (i) first sensor circuitry that is operative for measuring each electrical signal of the first plurality thereof; (ii) first communications circuitry configured to communicate with an external device; and (iii) a second housing for enclosing the first sensor circuitry and the first communications circuitry; wherein the first electronics module comprises one of the first plug and the first socket, and wherein the first detection module comprises the other one of the first plug and the first socket.

DETAILED DESCRIPTION

Figure 1A:
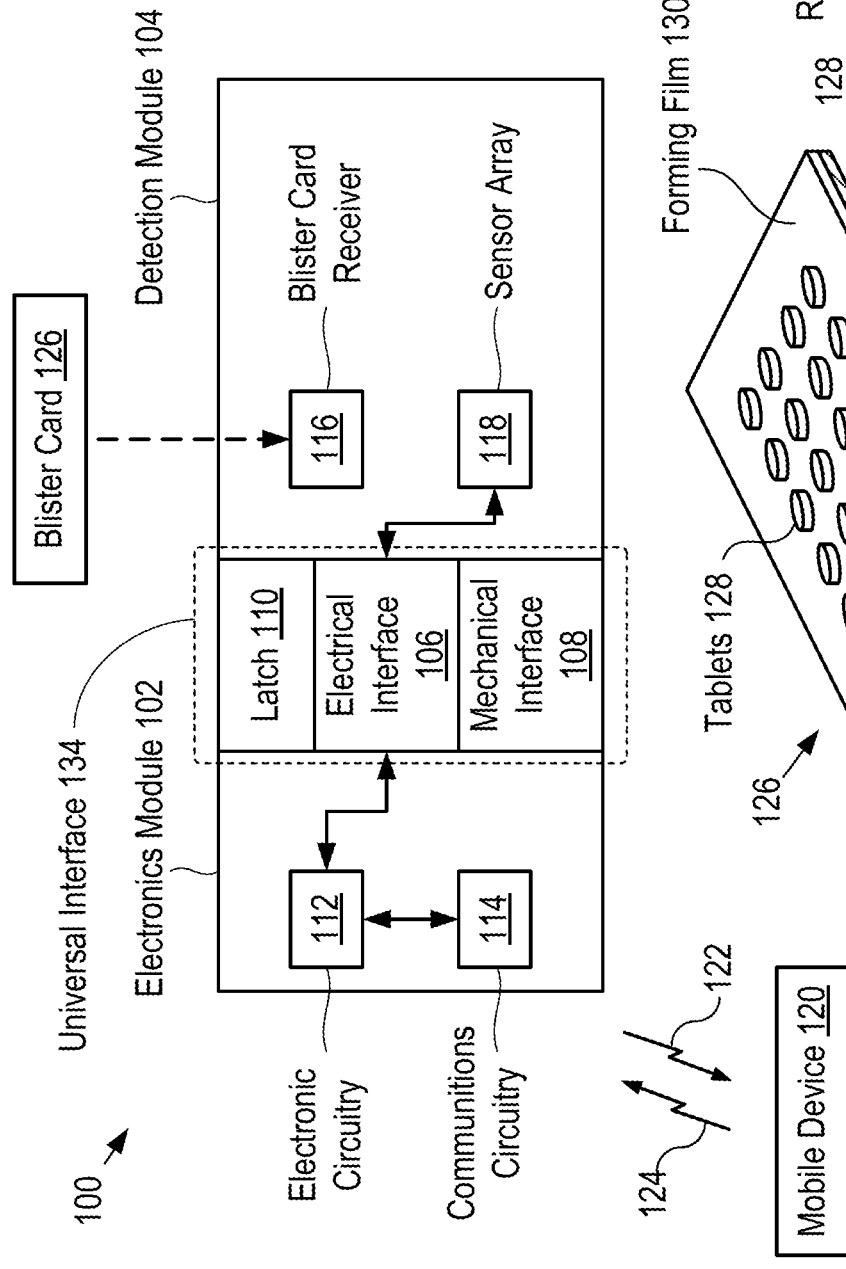
FIG. 1A depicts a functional block diagram of a modular medicine case in accordance with an illustrative embodiment in accordance with the present disclosure.

FIG. 1A depicts a functional block diagram of a modular medicine case in accordance with an illustrative embodiment in accordance with the present disclosure. Case 100 includes electronics module 102, detection module 104, electrical interface 106, mechanical interface 108, and latch 110. Case 100 is a modular smart case for tracking the state of blister card 126, which in the depicted example, is an OCP blister card. One skilled in the art will recognize, however, after reading this Specification, that the teachings of the present disclosure are applicable to myriad product tracking applications, such as consumer electronics, toys, healthcare and beauty care products (e.g., razor blades, etc.), foodstuffs, toner cartridges, and the like. Case 100, and its operation, is analogous to smart medicine cases described in U.S. Patent Publications 2016-0103085-A1 and 2017-0294105-A1, each of which is incorporated herein by reference.

Figure 1B:
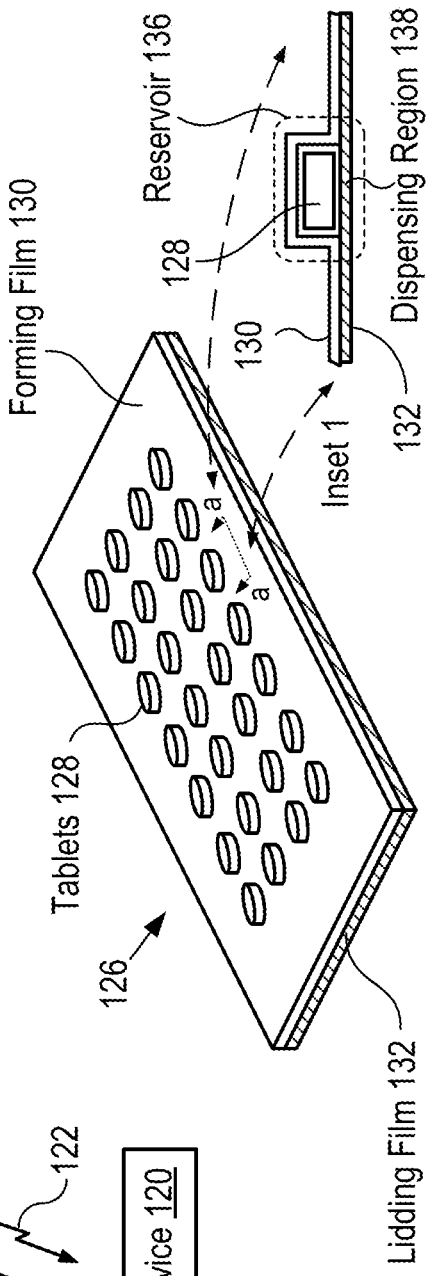
FIG. 1B depicts a schematic drawing of a perspective view of a blister card in accordance with the illustrative embodiment.

FIG. 1B depicts a schematic drawing of a perspective view of a blister card in accordance with the illustrative embodiment. A cross-section of one tablet region of the blister card is shown in Inset 1, where the cross-section is taken through line a-a of FIG. 1B.

Blister card 126 includes a plurality of tablets 128, each of which is contained within reservoir 136. Reservoir 136 is formed by forming film 130 and dispensing region 138, which is the region of lidding film 132 that forms the bottom of reservoir 136 and is the lidding-film portion through which tablet 128 is pushed when it is dispensed.

Forming film 130 is a layer of thermoformed plastic in which cavities for holding tablets 128 are formed.

Lidding film 132 is a thin sheet of aluminum foil. In some embodiments, lidding film 132 is a sheet of another electrically conductive material. In some embodiments, lidding film 132 includes a sheet of conductive material and a sheet of electrically insulating material, such as a paper sheet (with a printed calendar or instructions), polymer, etc. After tablets 128 are dispensed into the cavities of forming film 130, lidding film 132 is joined with the forming film to seal the cavities, thereby forming reservoirs 136, which enclose tablets 128. Typically, a calendar that describes the drug regimen is printed on the card and/or otherwise provided as part of the blister card.

The region of lidding film 132 that seals each cavity to form a reservoir defines dispensing region 138, through which its respective tablet 128 is dispensed by pushing the tablet through the lidding foil.

One skilled in the art will recognize that many types of medication are offered in a form suitable for packaging in a blister card, such as pills, capsules, lozenges, etc. For the purposes of this Specification, including the appended claims, the term "tablet" is used as a general term that encompasses all such medicinal forms.

Figure 2:
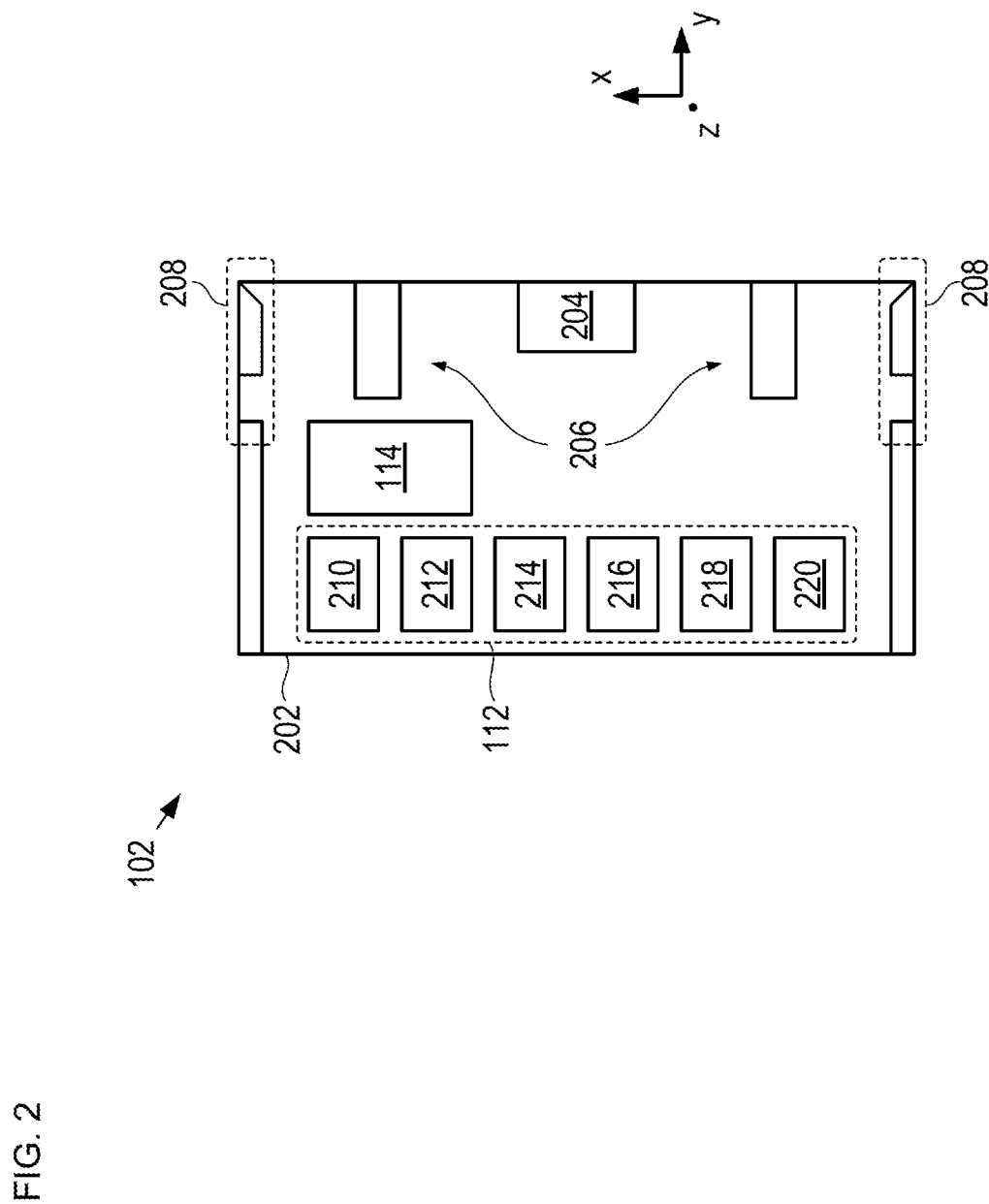
FIG. 2 depicts a schematic drawing of an electronics module in accordance with the illustrative embodiment.

FIG. 2 depicts a schematic drawing of an electronics module in accordance with the illustrative embodiment. Electronics module 102 includes housing 202, electronic circuitry 112, communications circuitry 114, socket 204, receivers 206, and catches 208.

Housing 202 is a conventional molded plastic housing configured to enclose electronics circuitry 112 and communications circuitry 114 in a substantially environmentally sealed environment.

Electronic circuitry 112 includes controller 210, memory 212, sensor circuit 214, power circuit 216, display circuit 218, and sleep-mode circuitry 220. The circuitry included in electronics circuitry 112 enable it to interface with the sensor array included in detection module 104, as well as receive and condition the output signals of each sensor (e.g., provide pre-amplification, digitization, etc.), provide power conditioning and management, display information to the user, etc.

Controller 210 is a conventional processor having signal processing and computation capabilities.

Memory 212 is a conventional memory module for storing information and data.

Sensor circuit 214 is configured to receive sensor signals from the sensor array of detection module 104 via electrical interface 106, measure the sensor signals to detect changes in the state of a blister card held in the detection module, and the like.

Power circuit 216 includes an energy-storage unit and power management circuitry. In the depicted example, the energy-storage unit is a rechargeable battery; however, a different energy-storage unit can be used in power circuit 216 without departing from the scope of the present disclosure. Energy-storage units suitable for use in embodiments in accordance with the present disclosure include, without limitation, non-rechargeable batteries, super capacitors, and the like. In some embodiments, power circuit 216 includes one or more energy-scavenging devices (e.g., solar cells, vibration harvesters, etc.) for passively recharging the energy-storage unit.

Display circuit 218 includes a status indicator and drive circuitry for the status indicator. In the depicted example, the status indicator is a simple light-emitting diode (LED); however, other status indicators, such as liquid-crystal displays, LED-based displays, speakers, buzzers, and the like, can be used in display circuit 218 without departing from the scope of the present disclosure.

Sleep-mode circuitry 220 includes low-power dissipation circuitry, a wake-up circuit, and a low-power-dissipation accelerometer. Sleep-mode circuitry 220 facilitates long battery life between charges by enabling an extremely low-power dissipation mode during periods of case inactivity. In response to an environmental stimulus, such as detection of activity by the accelerometer (e.g., shock and/or vibration associated with shaking the case, etc.), a wake-up signal received from external device 120, and the like, the wake-up circuit activates electronics circuitry 112 such that it operates in a conventional power-dissipation mode in which it can determine the state of the blister card located in detection module 104 and output its status to the user.

Communications circuitry 114 includes a wireless Bluetooth Low-Energy (BLE) transceiver for sending status signal 122 to external device 120 and receiving operational communications 124 from external device 120. In some embodiments, communications circuitry includes a different wired and/or wireless communications electronics, such as FireWire, USB, lightning connector, a dock connector, cellular, WiFi, near-field-communications (NFC) radio, optical links, etc.

In the depicted example, external device 120 is a smart phone that runs a software application (i.e., a mobile app) that provides assistance to the patient and/or caregiver to achieve and maintain good adherence to the prescribed drug regimen. In some embodiments, external device 120 communicates with a different device, such as a different mobile device, a computer and/or base station.

The case and smartphone app collectively determine the state of the blister card and provides a visual and/or audible indication of adherence. If failure to follow the regimen is detected, the smartphone contacts one or more people in the user's defined support group (e.g., a caregiver, spouse, child, doctor, etc.) to alert them that the user might require assistance.

Socket 204 is a conventional electrical socket that is a first portion of electrical interface 106. Socket 204 is configured to receive a plug disposed on detection module 104. Once the socket and plug are engaged, electrical communication between electronics circuitry 112 and sensor array 118 on the detection module is enabled.

Receivers 206 are a pair of conventional female mechanical connectors that collectively define a first portion of mechanical interface 108. Receivers 206 are configured to engage a pair of conventional male mechanical connectors included in detection module 104. In the depicted example, the receivers and male mechanical connectors are configured to enable only one orientation between the electronics and detection modules (i.e., they are "keyed") to ensure that the modules engage properly.

Catches 208 are mechanical structures that define a first portion of latch 110. Each of catches 208 is configured to engage a mating spring bolt that extend from the mating surface of detection module 104. Catches 208 reversibly locks the two modules together to form a fully assembled smart medicine case.

It should be noted that the configuration and capabilities of electronics module 102 described above is merely exemplary and that myriad alternative configurations having more or less electronics functionality can be used for the electronics module without departing from the scope of the present disclosure. For example, in some embodiments, electronics module 102 includes, without limitation:
  i. additional processing capability; or
  ii. onboard clock circuitry; or
  iii. energy scavenging systems, or
  iv. alternative or additional sensor interface circuitry; or
  v. alternative or additional on-case alerts (e.g., LCD displays, speakers, buzzers, etc.); or
  vi. environmental (e.g., touch, temperature, acceleration, humidity, shock, geolocation, etc.) sensors; or
  vii. any combination of i, ii, iii, iv, v, and vi.

One skilled in the art will recognize, after reading this Specification, that the design features of housing 100 are based on the particular arrangement of blister card 102, as well as the sensing technology used to monitor its state and, as provided herein, are merely exemplary. Myriad alternative design features are possible without departing from the scope of the present disclosure.

Figure 3:
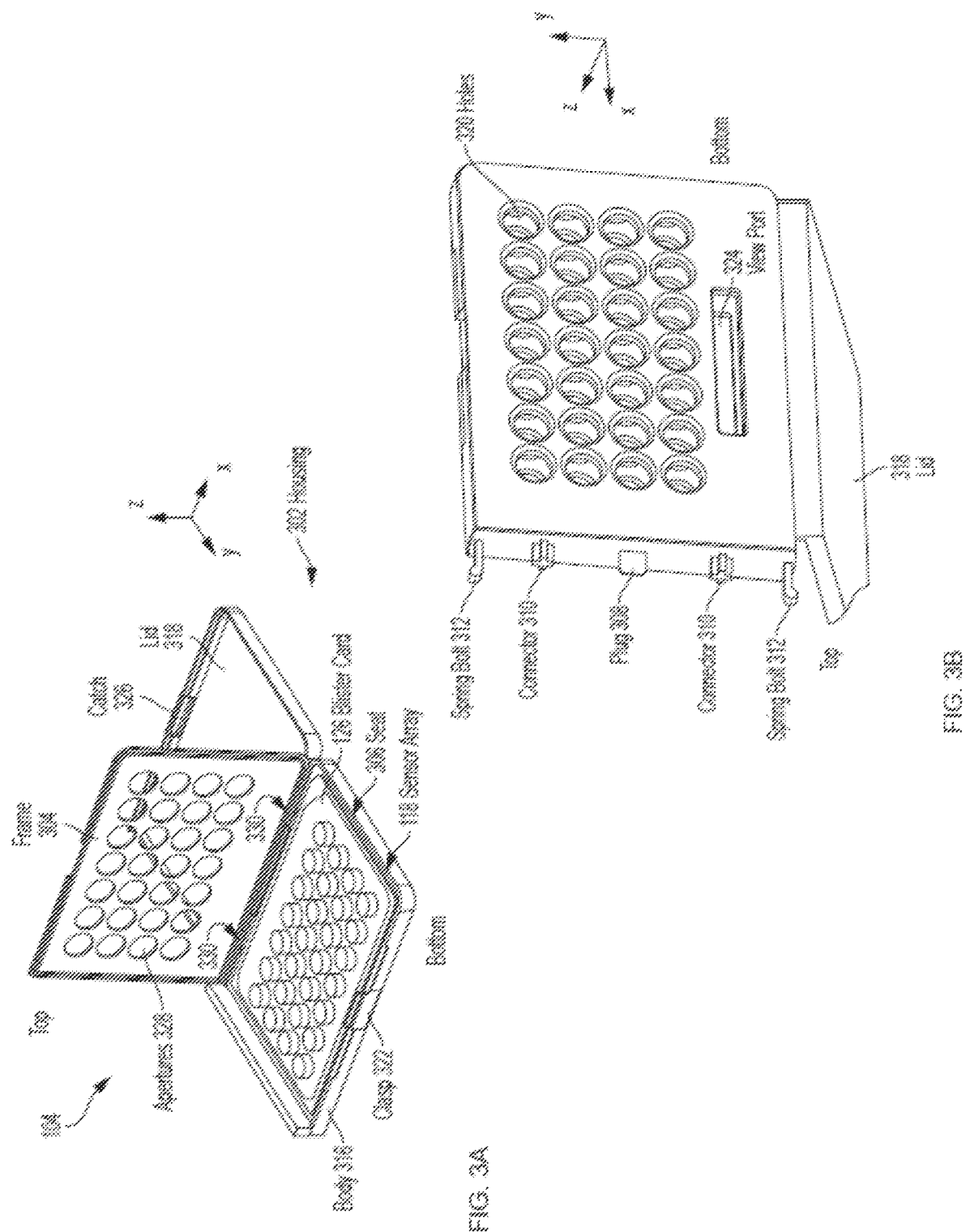
FIG. 3A-B depict schematic drawings of perspective views from the top and bottom sides of a detection module in accordance with the illustrative embodiment.

FIG. 3A-B depict schematic drawings of perspective views from the top and bottom sides of a detection module in accordance with the illustrative embodiment. Detection module 104 includes housing 302, receiver 116, sensor array 118, plug 308, connectors 310, and spring bolts 312.

Housing 302 is a conventional molded plastic housing comprising body 316 and lid 318.

Body 316 is a substantially rigid platen comprising an array of holes 320, clasp 322, and optional view port 324.

Each hole 320 is aligned with a different sensor of sensor array 118. The arrangement of holes 320 matches that of the arrangement of tablets in blister card 126, and the holes are configured to enable a tablet to pass through body 316 when dispensed.

View port 324 is an opening formed in body 316 to expose a portion of blister card 126 for viewing. View port 324 is optionally included to enable information printed on a blister card to be read through housing 302.

Lid 318 is a substantially rigid "clam shell" structure that includes catch 326, which engages clasp 322 when lid 318 is closed to hold the body and lid together.

Receiver 116 includes frame 304 and seat 306, which are collectively configured to locate blister card 126 such that each tablet location of the blister card is operatively coupled with a different sensor of sensor array 118 and a different one of holes 320.

Frame 304 is a substantially rigid plate comprising apertures 328, each of which exposes a different tablet of the blister card when the frame is locked in place. Frame 304 is connected to body 316 via conventional hinge 330, which allows the frame to rotate out of the way to enable installation of a blister card in the detection module and rotate back over the blister card to engage with a catch (not shown) that secures the frame and blister card to body 316.

Seat 306 is a recessed region of body 316 that is configured to accept blister card 126 and laterally position it to align its tablets with sensor array 118 and holes 320. In some embodiments, seat 306 is not included. In some embodiments, seat 306 is formed as part of frame 304.

Sensor array 118 is an array of sensors that is arranged in an arrangement that matches that of the tablets included in blister card 126. Sensor array 118 (not seen in FIGS. 3A-B) resides between body 316 and blister card 126 such that each of its sensors is operatively coupled with a different tablet site when the blister card is secured in housing 302.

Figure 4:
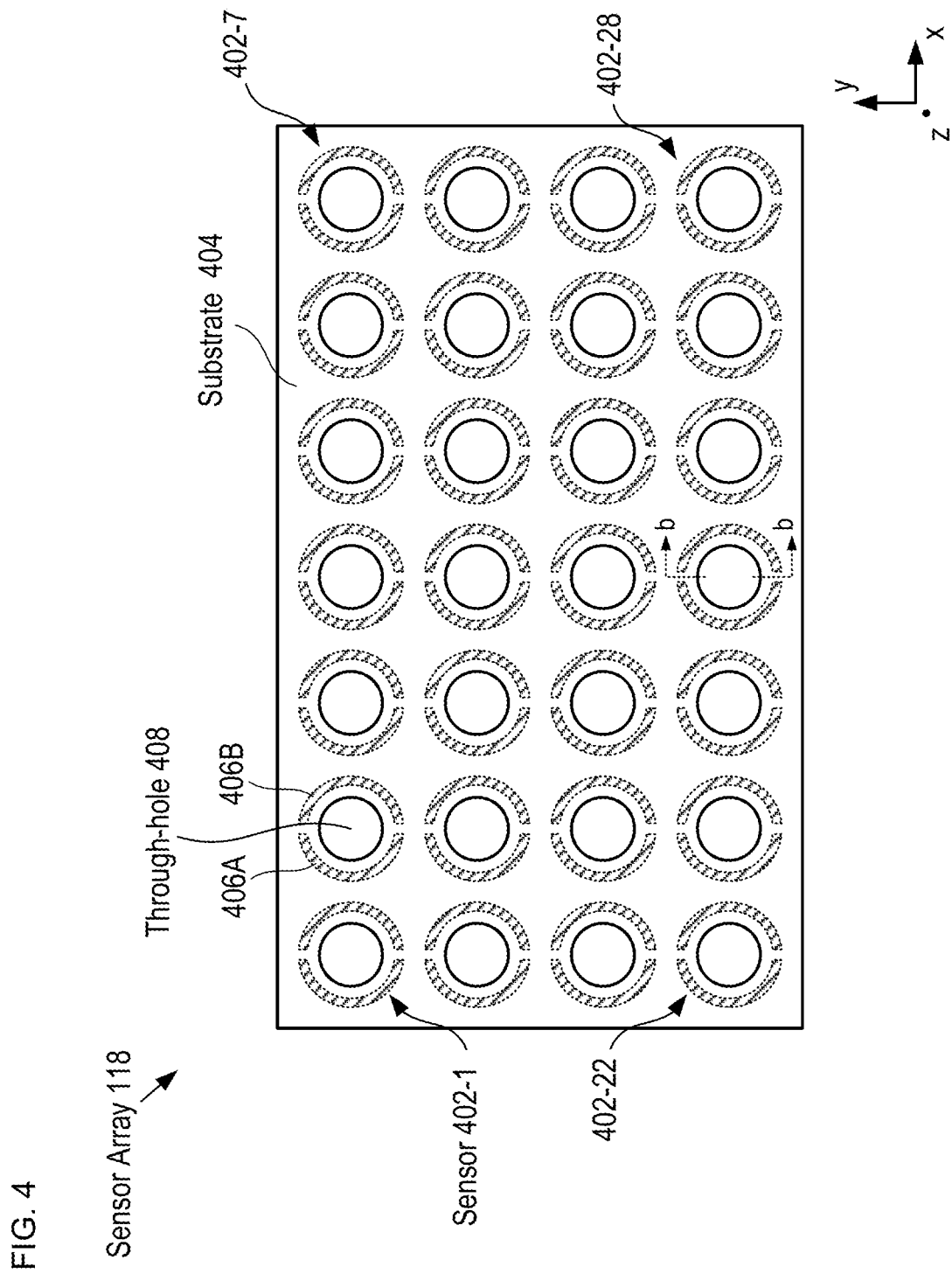
FIG. 4 depicts a schematic drawing of a top view of a sensor array in accordance with the illustrative embodiment.

FIG. 4 depicts a schematic drawing of a top view of a sensor array in accordance with the illustrative embodiment. Sensor array 118 comprises capacitance sensors 402-1 through 402-28, which are formed in substrate 404 such that they have the same arrangement as tablets 128.

Each of sensors 402-1 through 402-28 (referred to, collectively, as sensors 402) includes electrodes 406A and 406B, which are formed within substrate 404. In the depicted example, sensors 402 are capacitance sensors that are arranged in a 4×7 array. Although sensor array 118 employs capacitive sensing technology to monitor the state of blister card 126, many alternative sensing technologies can be employed in detection module 104 without departing from the scope of the present disclosure. Sensing technologies suitable for use in embodiments in accordance with the present disclosure include, without limitation, strain sensing, optical sensing, acoustic sensing, and tactile sensing, among others.

Substrate 404 is a conventional printed-circuit board (PCB) through which through-holes 408 are formed. Through-holes 408 extend through substrate 404 to allow for the passage of each of the tablets of blister card 126 through detection module 104 when it is dispensed from the blister card. In some embodiments, substrate 404 comprises a flexible material or is incorporated into a different surface of case 100 (e.g., its lid, back surface, etc.) by, for example, embedding components into the material of housing 302, printing electronic elements on the surface itself, and the like.

Electrodes 406A and 406B are disposed within substrate 404 such that they collectively substantially surround through-hole 408. In operation, electrodes 406A and 406B are positioned in close proximity to the portion of lidding film 132 located beneath their respective tablet 128.

Figure 5A:
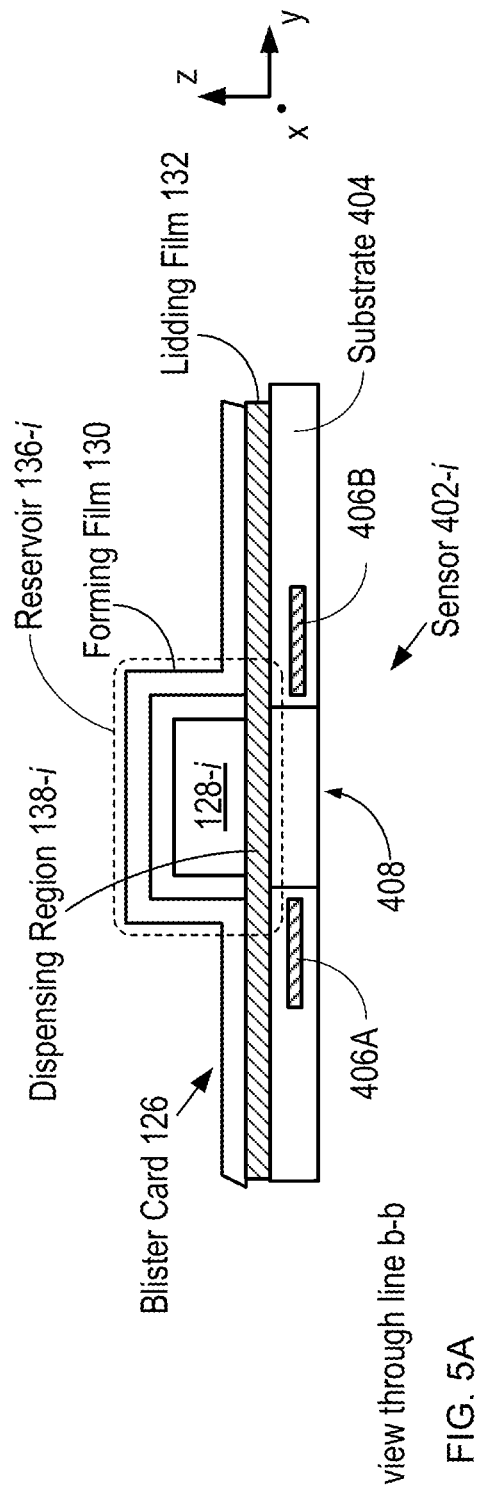
FIG. 5A depicts a schematic drawing of a cross-sectional view of a sensor of sensor array 118 in an operatively coupled arrangement with a tablet region of blister card 126.

FIG. 5A depicts a schematic drawing of a cross-sectional view of a sensor of sensor array 118 in an operatively coupled arrangement with a tablet region of blister card 126. The view depicted in FIG. 5A is taken through line b-b of FIG. 4.

Sensor 402-$i$ includes electrodes 406A and 406B, which are formed within the body of substrate 404 such that, when blister card 126 is in contact with sensor array 118, the capacitance between the electrodes of each sensor 402-$i$ is significantly affected by the state dispensing region 138-$i$, which is the region of lidding film 132 that forms the bottom of reservoir 136-$i$.

In each sensor 402-$i$, the conductive material (i.e., lidding film 132) of its dispensing region 138-$i$ forms fringing fields with its electrodes 406A and 406B. These fringing fields impact the capacitance of the capacitive sensor giving it a first value when the dispensing region is intact. When tablet 128-$i$ is dispensed, however, the breakage of dispensing region 138-$i$ changes the physical configuration between the lidding film material and electrodes 406A and 406B, which affects the fringing fields and, therefore, the capacitance of sensor 402-$i$. It should be noted that the capacitance of sensor 402-$i$ changes whether or not the material of dispensing region 138-$i$ breaks away entirely or pieces of it remain hanging in hole 408 thereafter. It should also be noted that such capacitive change is operative for a lidding film 132 comprising a multilayer of materials (i.e., combinations of metal, paper and/or plastic), be the individual layers electrically conductive or not—the latter of which (even though electrically not biased) affects the effective dielectric constant in the gap between the sensing electrodes 406A and 406B.

To sense the capacitance of each sensor 402-$i$, lidding film 132 is typically electrically grounded, while each electrodes 406A and 406B is connected to a high-impedance sense circuit. In some embodiments, lidding film 132 is left electrically "floating;" however, grounding the lidding film is preferable because it provides improved sense-signal stability and noise immunity. Unfortunately, sensors 402 can be sensitive to external noise and interference, such as stray or parasitic capacitances, electromagnetic interference (EMI), and the like.

In some embodiments, in order to mitigate the effects of noise and interference, electrodes 406A and 406B are segmented into more than two circumferential sections. Using such electrode configurations, capacitive sensing is implemented by monitoring the change in the capacitance between the electrode segments, which is still affected by fringing fields between the electrode segments and the aluminum foil over the hole. Unfortunately, while segmenting electrodes 406A and 406B provides some measure of noise immunity, noise and interferences can still be a problem.

Figure 5B:
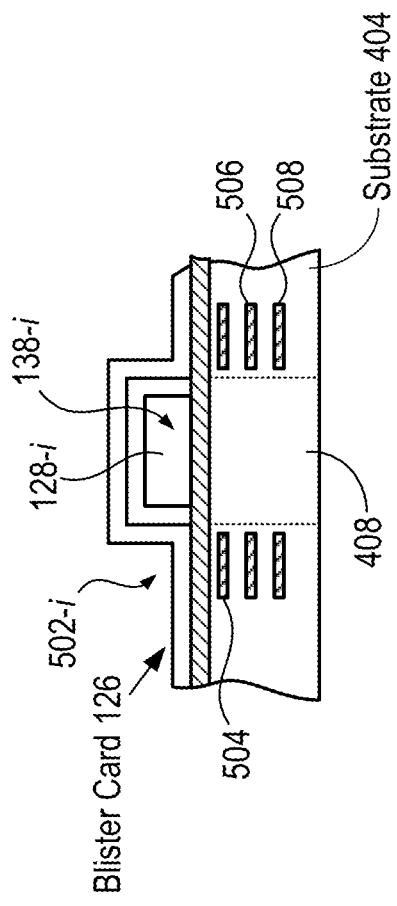
FIG. 5B depicts a schematic drawing of a cross-sectional view of an alternative capacitance sensor in accordance with the present disclosure.

FIG. 5B depicts a schematic drawing of a cross-sectional view of an alternative capacitance sensor in accordance with the present disclosure. Sensor 502-$i$ is suitable for use in detection module 104 and comprises substrate 404, electrodes 504, 506 and 508. Sensor 502-$i$ has significantly improved noise immunity as compared to sensor 402.

Each of electrodes 504, 506 and 508 is a ring electrode that is formed within substrate 404 such that they are parallel. Electrode 504 and 506 are located between lidding film 132 and electrode 508. Electrodes 504 and 506 collectively define a first parallel-plate capacitor within substrate 404. Additional capacitances are available from pair-wise combinations of lidding film 132 and electrodes 504, 506 and 508.

For example, electrodes 504 and 506 can operate as a sense capacitance that is sandwiched between lidding film 132 and electrode 508, which shield this sense capacitance from noise and interference emanating from above blister card 102 and below body 316.

The initial value of the sense capacitance arising from electrodes 506 and 508 is determined by the mutual capacitance between these electrodes.

The sense capacitance arising from electrodes 504 and 506 is affected by the physical configuration of dispensing region 138-$i$.

Dispensing a tablet results in breaking dispensing region 138-$i$. As the tablet is pushed out, this broken portion of the lidding film deflects into hole 408, affecting the sense capacitance comprising electrodes 504 and 506.

The sense capacitance arising from electrodes 504 and 506 is also characterized by a substantially fixed capacitance resulting from their parallel overlap within substrate 404.

The operation of sensor 502-$i$ is analogous to that of sensor 402-$i$; however, the fringing-field capacitances of sensor 502-$i$ are shielded from stray capacitances, due for example to those from human touch.

In some embodiments, additional shielding is provided for sense electrodes 504 and 506 by adding shielding lines that surround each sense electrode in its plane within substrate 404.

Each of sensors 402 is electrically connected to sensing circuitry in electronics module 102 via electrical traces (not shown for clarity) and electrical interface 106. As a result, each sensor can be monitored individually to enable specificity of the dispensing of each tablet 128 in blister card 126. In some embodiments, sensors 402 are electrically connected and interrogated using a row/column addressing scheme.

OCP represents one of many applications in which it is critical to be able to identify which tablet has been dispensed during a dispensing event. The hormonal content of each tablet is dependent on the day during the blister card's use cycle. One skilled in the art will recognize, however, after reading this Specification, that not all medication requires the ability to uniquely identify the identity of a tablet that has been dispensed and, as a result, the sensing approach used to detect tablet dispensing can be greatly simplified. For example, in some cases, all of the tablets of a blister card are substantially identical. In some embodiments in accordance with the present disclosure, therefore, all of sensors 402 are electrically connected in parallel or serially and specificity for which tablet 128 is dispensed is not enabled. In some such embodiments, a single sensor is used to detect dispensing events, such as an accelerometer operatively coupled with the blister card, a single capacitive sensor that spans all the tablet sites such that each dispensing event is indicated by a change in the capacitance of this solitary capacitor.

Alternatively, in some embodiments, row/column sensing is simplified to row or column sensing wherein, for example, one electrode of a capacitive sensor is common to an entire row or column of tablet locations, while the other electrode is divided into site-specific individual electrodes.

In such embodiments, exhaustion of a blister card (which denotes a refill is due) can be detected in numerous ways, such as simply tracking the dispensing events and comparing their count to the total count of the tablets on the blister card as provided or monitoring of the total magnitude of the sensor output signal change with dispensing events and comparing the result with a reference magnitude change determined, for example, by prior calibration operation.

In some embodiments, if exhaustion of the blister card is detected, an alert is sent to the user and/or the user's care circle to warn them that the blister card is now empty. In some embodiments, this warning is generated when the number of tablets in the blister card has dropped to a threshold level so as to initiate a refill reminder to the user or user's care circle, or generate a refill request directly to the pharmacy.

In many capacitive sensing embodiments, it is often desirable to provide electrical shielding implementations to reduce, if not eliminate, parasitic effects. By extension it may at times be advantageous to further shield parasitic capacitances (e.g., those that arise from the user touching these case) by incorporating a conductive shield (that is electrically isolated from substrate 404) into the bottom surface of the case under the area the pill card is received. Such shielding can be achieved in many ways, such as using conductive paint on the backside of the case and/or the inside surface of the underside over which substrate 404 is placed. Other suitable approaches employ a thin metallic film (e.g., aluminum foil) in these locations. In operation, such shields would typically be connected to the electrical ground of the circuitry included in case 100.

It should be noted that sensing approaches other than the use of a dedicated sensor for each tablet location can be used in embodiments in accordance with the present disclosure.

For example, several approaches for blister-pack monitoring based on the use of electrical impedance tomography (EIT) are described in U.S. patent application Ser. No. 14/879,874, filed Oct. 9, 2015 (Attorney Docket: 3005-002US1), which is incorporated herein by reference. Such approaches are suitable for use in sensing the rupture of a dispensing region 138 and its location within blister card 126. Using EIT, the resistance (or impedance) of a dispensing region 138 can be detected by monitoring its impedance distribution via electrical contacts located at the periphery of the blister card.

Figure 5C:
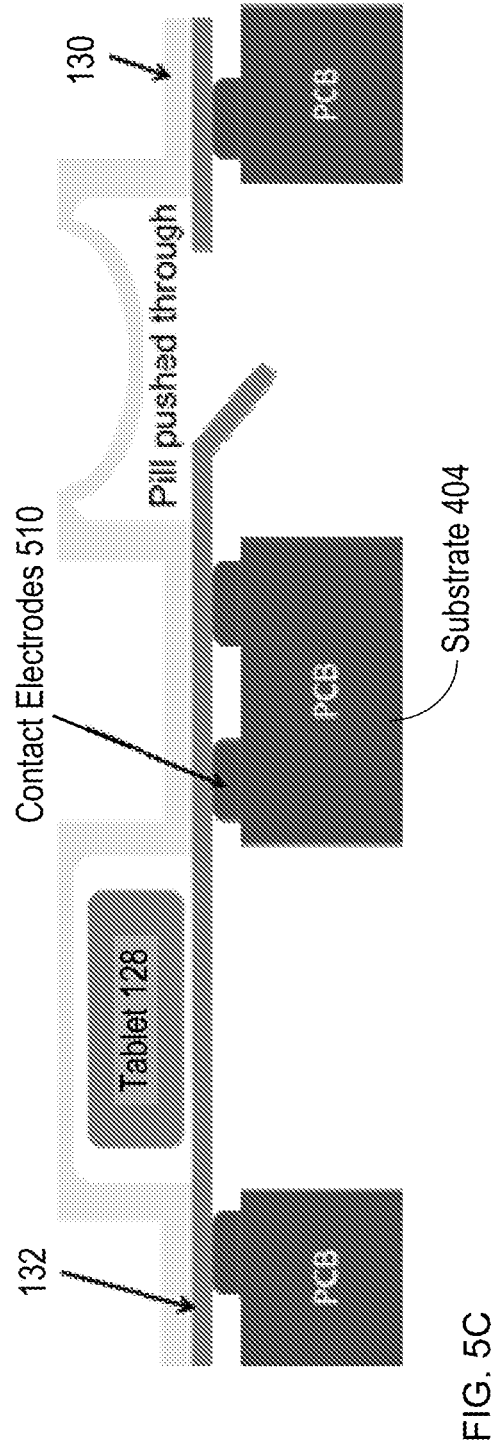
FIG. 5C depicts a schematic drawing of a cross-section of a region of a detection module configured to monitor the state of a blister card via EIT.

FIG. 5C depicts a schematic drawing of a cross-section of a region of a detection module configured to monitor the state of a blister card via EIT.

Contact electrodes 510 can be realized using the top PCB metal layer of substrate 404. To further facilitate contact to the lidding film of the blister card, the electrodes can include solder disposed on their top surfaces. Alternatively, the electrode may incorporate external components assembled on the PCB to facilitate contact.

Figure 5D:
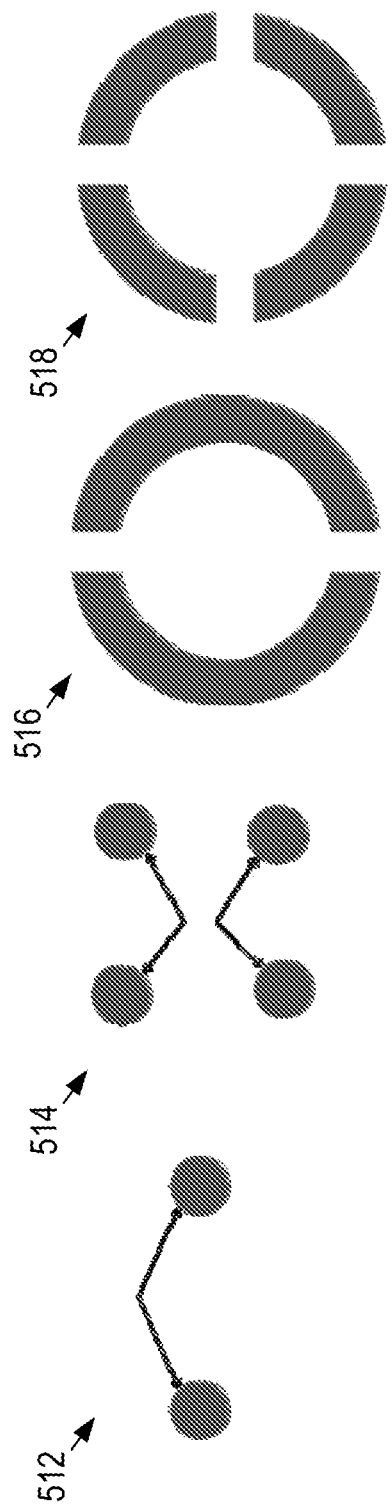
FIG. 5D depicts examples of electrode shapes and arrangements suitable for use in contact electrodes 510.

FIG. 5D depicts examples of electrode shapes and arrangements suitable for use in contact electrodes 510. Electrode arrangements 512 and 516 enable simple resistance or impedance measurement between the electrodes to enable them to sense a break in lidding film 132 between them. Electrode arrangements 514 and 518 enable four-point probe measurements across a dispensing region 138. It should be noted that the shapes and arrangements shown in FIG. 5D represent only a few examples in accordance with the present disclosure. The shape, size, number and arrangement of contact electrodes can be optimized for a desired sensing sensitivity and reliability, as well as sensing power consumption considerations.

In some embodiments, an alternative sensing technique is employed, wherein one or more electrical switches are disposed at or near the periphery of each hole. As a pill is pushed through a hole, the switches provide a signal that indicates a pill has been dispensed. In some embodiments, the switches are permanently latching to provide a permanent indication of which pills have been dispensed.

Returning now to FIGS. 3A-B, plug 308 is a male electrical connector that mates with socket 204 to electrically couple electronics module 102 and detection module 104. Plug 308 and socket 204 collectively define electrical interface 106. Although plug 308 is included in detection module 104 and socket 204 is included in electronics module 102 in the depicted example, in some embodiments, the locations of these components is reversed. In other words, in some embodiments, plug 308 is included in electronics module 102 and socket 204 is included in detection module 104. Furthermore, myriad designs for socket 204 and plug 308 can be used in accordance with the present disclosure without departing from its scope.

Connectors 310 are male mechanical connectors that mate with receivers 206 to align electronics module 102 and detection module 104. Typically, connectors 310 and receivers 206 enable only one orientation of the electronics and detection modules to ensure their proper alignment. Connectors 310 and receivers 206 collectively define mechanical interface 108. Although connectors 310 are included in detection module 104 and receivers 206 are included in electronics module 102 in the depicted example, in some embodiments, the locations of these components is reversed. In other words, in some embodiments, connectors 310 are included in electronics module 102 and receivers 206 are included in detection module 104. Furthermore, myriad designs for connectors 310 and receivers 206 can be used in accordance with the present disclosure without departing from its scope.

Each of spring bolts 312 is a resilient element that is configured to reversibly engage catch 208 to lock the electronics module 102 and detection module 104 together. Spring bolts 312 and catches 208 collectively define latch 110. In the depicted example, to detach the modules, spring bolts 312 are depressed to disengage them from catches 208, thereby enabling the separation of electronics module 102 and detection module 104. Although spring bolts 312 are included in detection module 104 and catches 208 are included in electronics module 102 in the depicted example, in some embodiments, the locations of these components is reversed. In other words, in some embodiments, spring bolts 312 are included in electronics module 102 and catches 208 are included in detection module 104. Furthermore, myriad designs for catches 208 and spring bolts 312 can be used in accordance with the present disclosure without departing from its scope.

As noted above, electrical interface 106, mechanical interface 108, and latch 110 collectively define a universal interface (i.e., universal interface 134) that enables electronics module 102 to be operatively coupled with any of a plurality of detection module designs in reversible fashion.

Figure 6A:
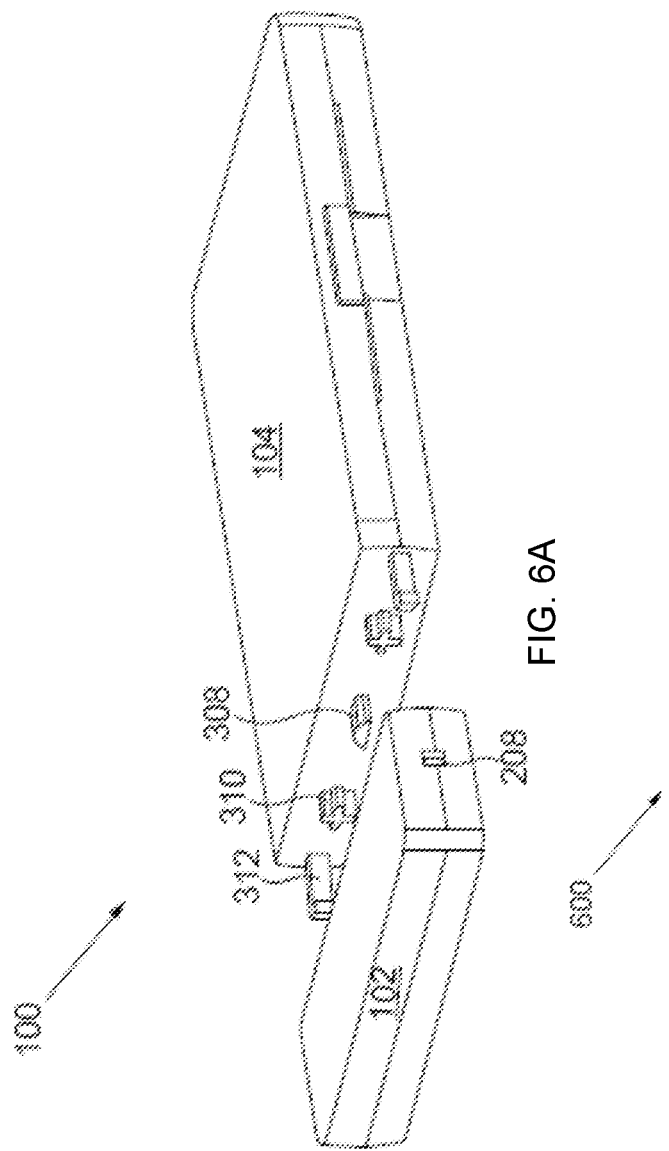
FIG. 6A depicts an image showing electronics module 102 and detection module 104 in a disengaged state in accordance with the illustrative embodiment.

FIG. 6A depicts an image showing electronics module 102 and detection module 104 in a disengaged state in accordance with the illustrative embodiment.

Figure 6B:
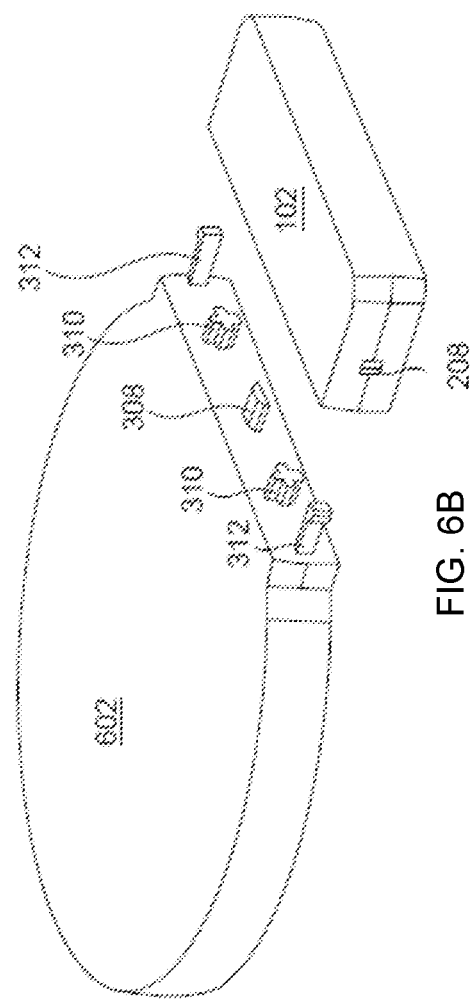
FIG. 6B depicts an image showing an alternative configuration of a modular medicine case in accordance with the present disclosure.

FIG. 6B depicts an image showing an alternative configuration of a modular medicine case in accordance with the present disclosure. Case 600 includes electronics module 102 and detection module 602, which are depicted in a disengaged, but aligned, configuration. In the depicted example, detection module 602 is a detection module configured for monitoring the state of a 28-day OCP blister card having a circular format.

Figure 7:
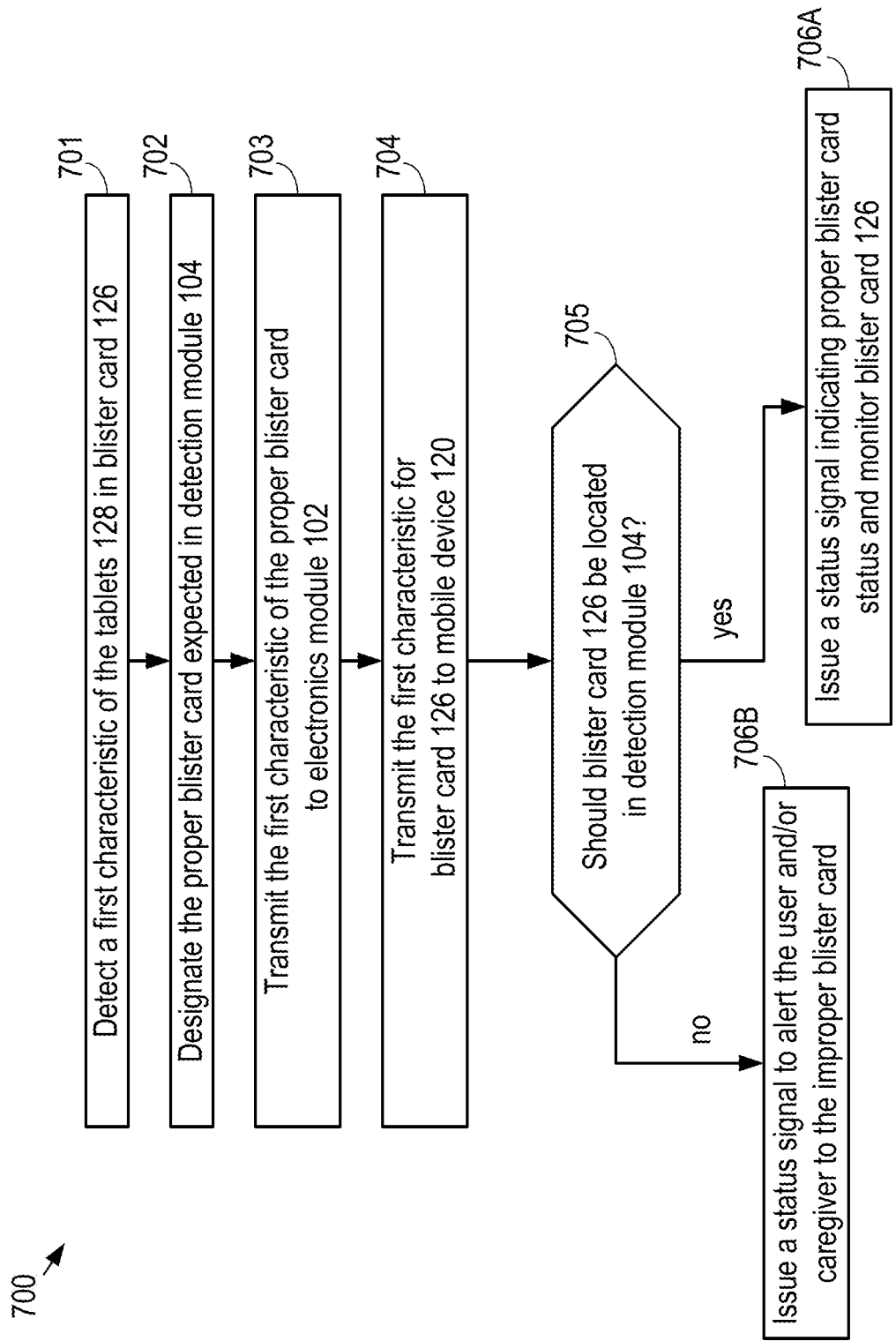
FIG. 7 depicts operations of a method suitable for identifying a detection module when it is engaged with an electronics module.

FIG. 7 depicts operations of a method suitable for identifying a detection module when it is engaged with an electronics module.

Method 700 begins with operation 701, wherein electronics module 102 detects a first characteristic for the blister card located in detection module 104. In the depicted example, first characteristic is the number of tablets included in the blister card, which is identified by detecting the number of sensors 402 present in detection module 104. Since the sensors are co-located with the holes through which the pills are dispensed, the number of intended blisters/pills should correspond to the number of sensors in the detection module. In some embodiments, the first characteristic is the arrangement of tablets 128 in blister card 126.

At operation 702, the user enters the type of blister card expected to be contained in detection module 104. Typically, this is done through external device 120, via an input device included in case 100, or via some combination thereof.

At operation 703, electronics module 102 receives the physical characteristics of the blister card expected to be in the detection module from external device 120.

At operation 704, electronics module 102 transmits the first characteristic identified for blister card 126 to external device 120.

At operation 705, the first characteristic identified for blister card 126 is compared to the first characteristic for the expected blister card to verify whether the appropriate blister card is located in detection module 104. In some embodiments, this verification is performed by an application on the external device. In some embodiments, the verification is performed by electronics module 102. In some embodiments, verification is performed cooperatively by the external device and the electronics module.

If the verification confirms that the detection module contains the correct blister card, method 700 proceeds to operation 706A wherein blister card 126 is monitored.

If, on the other hand, it is determined that the wrong blister card is located in detection module 104, method 700 continues to operation 706B, wherein an alert is generated by electronics module 102 and/or external device 120 denoting the inconsistency. In some embodiments, the alert is provided to the user. In some embodiments, the alert is provided to the user and/or a member of the user's care circle.

In some embodiments, detection module 104 incorporates indictors that enable electronics module 102 to identify the actual brand of the blister card for which it is intended. In one exemplary approach, the indicators include passive electrical components realized from the PCB metal layers, such as resistors and capacitors. In some embodiments, the identification is accomplished by checking one or more of:

i. the value of such indicators; or
    ii. metal layer or layers on which such indictors are placed; or
    iii. circuit characteristics of how such indictors may be interconnected; or
    iv. any combination of i, ii, and iii.

Such indicators facilitate, for example, identification of counterfeit detection modules produced by third parties. In some embodiments, the electronics module refuses recognition of a detection module when the embedded indicators cannot be authenticated. In some embodiments, electronics module 102 incorporates one or more indicators to be authenticated by the accompanying mobile application. These indicators can be realized from the electronics module's hardware, firmware, or a combination of both. In some embodiments, electronics module 102 authenticates the accompanying mobile application being run by external device 120 via software indicators incorporated in the application.

In some embodiments, detection module 104 includes additional electronics functionality via incorporation of memory electronics to store identification data, intended brand information (e.g., a blister card's physical characteristics data, etc.), a preamplifier to facilitate better signal quality from sensor 402, an analog-to-digital convertor to improve data from the sensors by digitizing the signals on the detection module before they are passed to the electronics module, and the like. While such additions add incremental cost to the detection module, the additional cost is still low when compared to the components of the electronics module.

In many situations, a patient requires two or more medications that must be taken in adherence with a strict regimen. In accordance with the present disclosure, a plurality of smart pill cases can be combined into a single unit.

Figure 8:
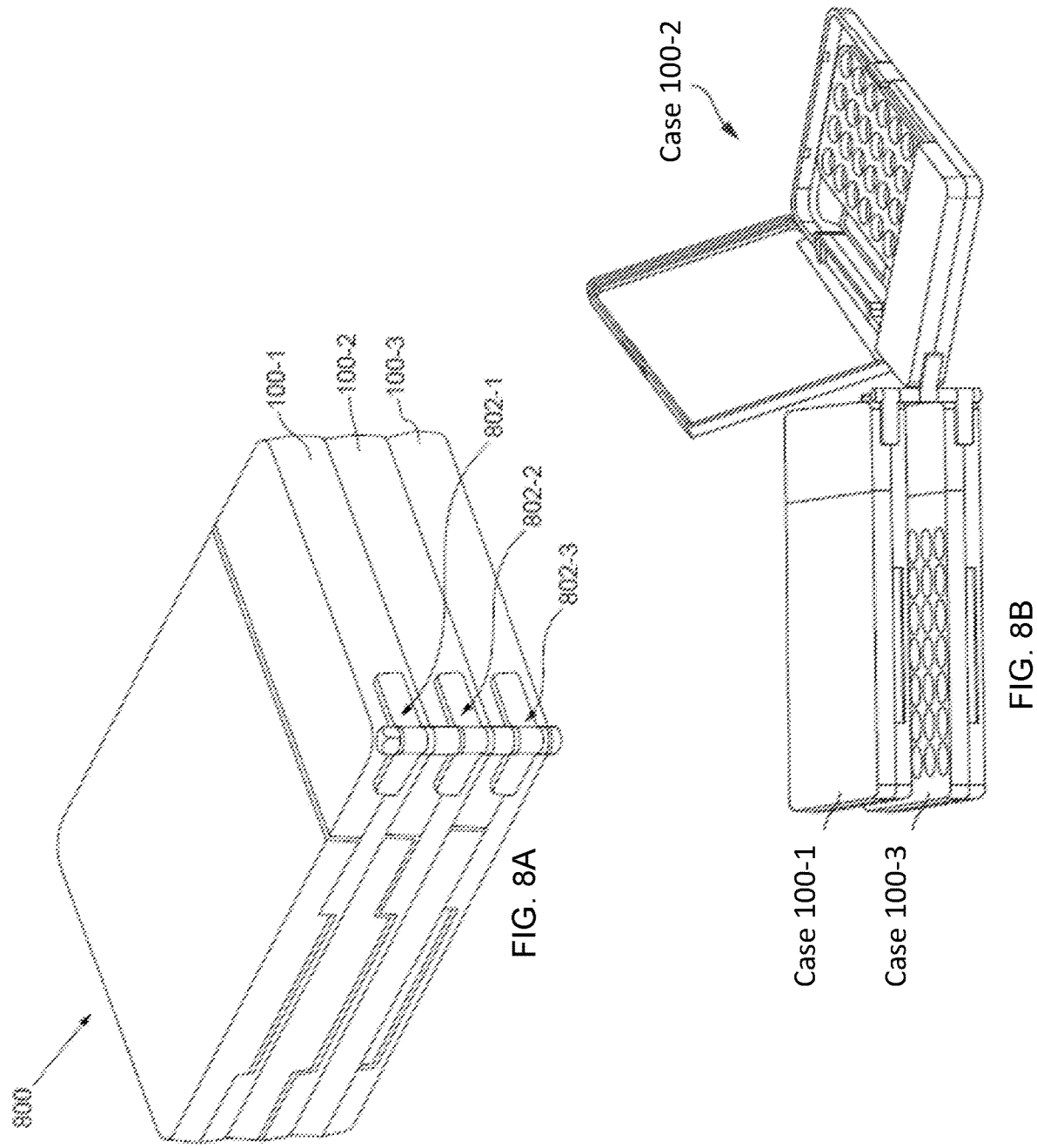
FIGS. 8A-B depict schematic drawings of perspective views of a multi-prescription smart medicine case, before and after the opening of one of the cases, respectively, in accordance with the present disclosure.

FIGS. 8A-B depict schematic drawings of perspective views of a multi-prescription smart medicine case, before and after the opening of one of the cases, respectively, in accordance with the present disclosure. Case 800 includes cases 100-1, 100-2, and 100-3 and hinges 802-1, 802-2, and 802-3.

Each of cases 100-1, 100-2, and 100-3 is substantially identical to case 100 described above.

Each of hinges 802-1, 802-2, and 802-3 is a conventional rotary hinge that is extendable such that case 800 can accommodate any practical number of cases 100. To open an individual case, that case is rotated out of alignment with the other cases to afford sufficient room to open its lid. In some embodiments, detents are included in the hinge design to establish the final position of a rotated case. In some embodiments, a hinge is spring-loaded to provide a self-powered swinging action.

In the depicted example, hinges 802-1, 802-2, and 802-3 are located at a corner of the electronics module; therefore, it does not interfere with the opening/closing of any individual case.

One skilled in the art will recognize, after reading this Specification, that myriad designs for enabling incorporation of multiple cases, while allowing for individual case access, are within the scope of the present disclosure.

Figure 9:
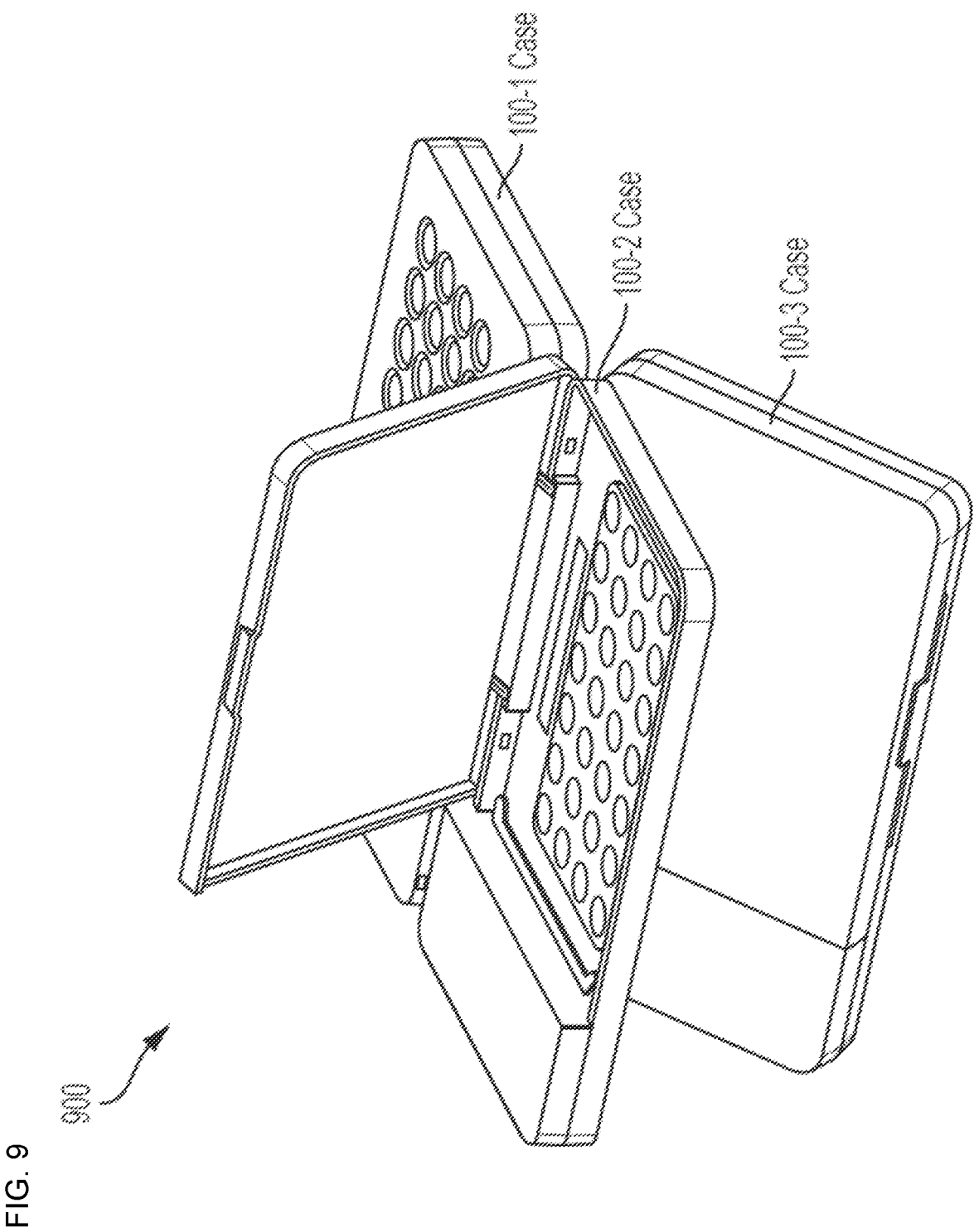
FIG. 9 depicts a schematic drawing of a perspective views of an alternative example of a multi-prescription smart medicine case in accordance with the present disclosure.

FIG. 9 depicts a schematic drawing of a perspective views of an alternative example of a multi-prescription smart medicine case in accordance with the present disclosure. Case 900 includes hinges (not shown) that enable the case to operate in a "laptop style". In the depicted example, the hinges are located on the side of the electronics modules to avoid interference with the opening of individual cases. Friction is typically used to maintain the rotational position of the hinges.

In some embodiments, a single electronics module is used to interface to a plurality of detection modules. Such embodiments provide a cost advantage over multi-case embodiments that include an electronics module for every detection module.

Figure 10A:
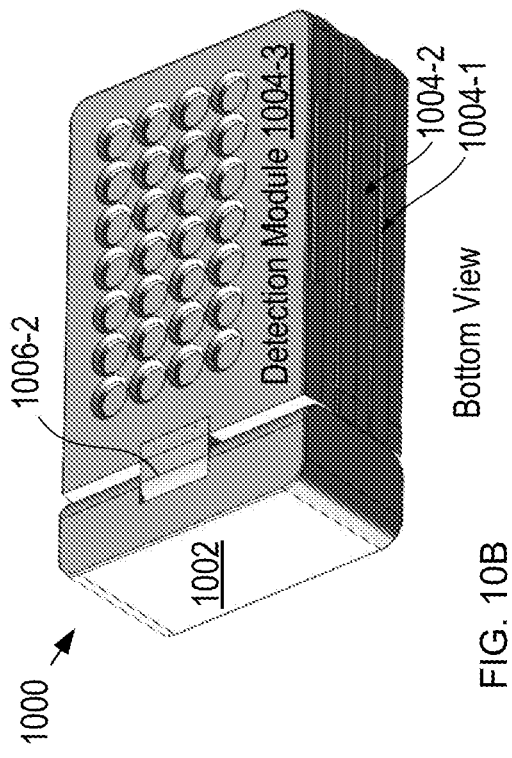
FIGS. 10A-B depicts schematic drawings of perspective views of the top and bottom, respectively, of another alternative example of a multi-prescription smart medicine case in accordance with the present disclosure.
Figure 10C:
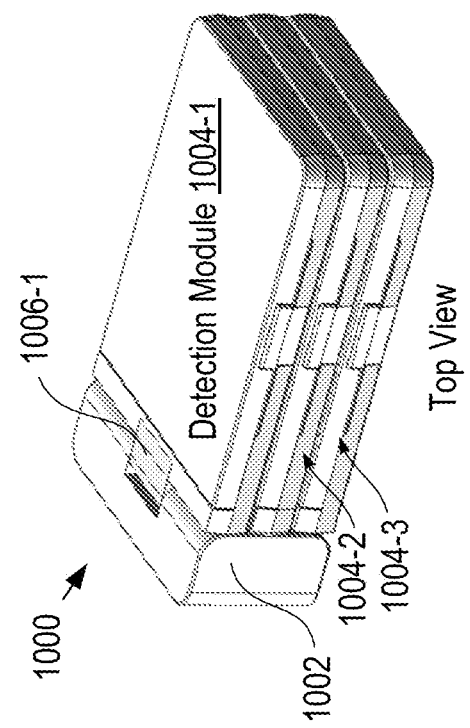
FIG. 10C shows a simplified view of the flex-circuit connections between rotating connectors 1006 and PCB 1012, which is included in electronics module 1002.
Figure 10B:
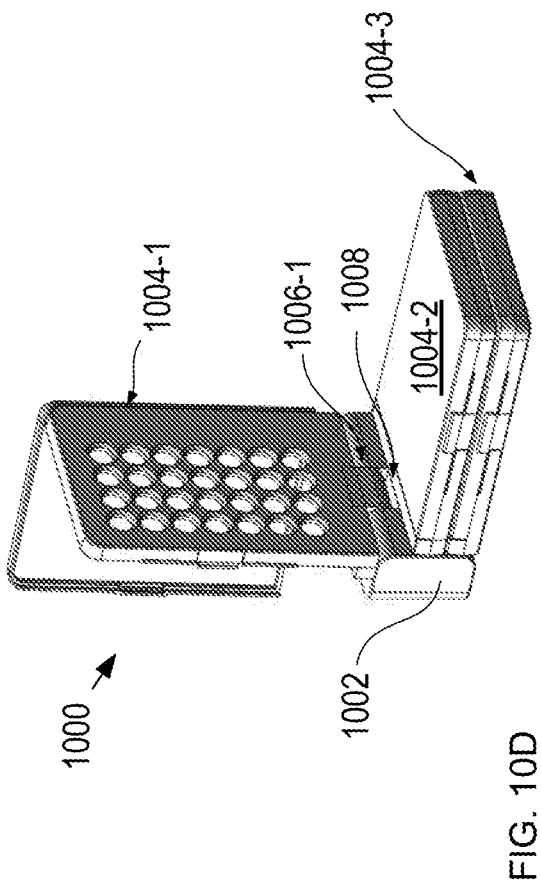

FIGS. 10A-B depicts schematic drawings of perspective views of the top and bottom, respectively, of another alternative example of a multi-prescription smart medicine case in accordance with the present disclosure. Case 1000 includes electronics module 1002, detection modules 1004-1 through 1004-3, rotating connectors 1006-1 and 1006-2, and fixed connector 1008.

Electronics module 1002 is analogous to electronics module 102; however, electronics module 1002 includes rotating connectors 1006-1 and 1006-2, and fixed connector 1008, which enables it to electrically couple with up to three detection modules.

Detection modules 1004-1 through 1004-3 are analogous to detection module 104; however, detection modules 1004-1 through 1004-3 are designed to mate with connectors 1006-1, 1008, and 1006-2, respectively, which enables it to electrically couple with three detection modules.

Rotating connectors 1006-1 and 1006-2 are configured to function as both mechanical and electrical interfaces for each of detection modules 1004-1 and 1004-3. Each rotating connector is designed to enable its respective detection module to rotate away from detection module 1004-2, thereby enabling access to the blister pack contained in any of the detection modules.

In similar fashion, fixed connector 1008 is configured to function as both mechanical and electrical interfaces for detection module 1004-2, which does not need to rotate out of its quiescent position.

In the depicted example, rotating connectors 1006-1 and 1006-2 are connected to electronics module 1002 via flexible electrical ribbon cables, which provide articulation of the connectors when desired.

FIG. 10C shows a simplified view of the flex-circuit connections between rotating connectors 1006 and PCB 1012, which is included in electronics module 1002.

Flex cables 1010-1 and 1010-2 are connected to rotating connectors 1006-1 and 1006-2 at their distal ends, while their proximal ends are connected to PCB 1012. It should be noted that the number of cables originating from PCB 1012 is dependent on the maximum number of detection modules that can be accommodated in case 1000. The lengths of flex cables 1010-1 and 1010-2 are selected according to the requisite articulation range of their respective detection modules.

Figure 10D:
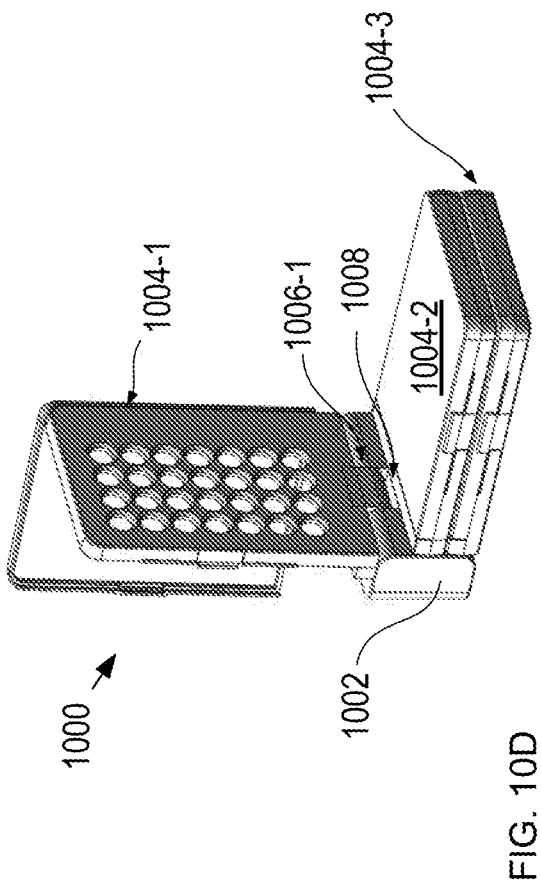
FIG. 10D depicts case 1000 with detection module 1004-1 in a rotated position and opened to afford access to its blister card.

FIG. 10D depicts case 1000 with detection module 1004-1 in a rotated position and opened to afford access to its blister card. With detection module 1004-1 rotated away, access to detection module 1004-2 is enabled. In the depicted example, detection module 1004-3 is rotated in the opposite direction to that of detector module 1004-1 to enable access to its content.

Figure 11A:
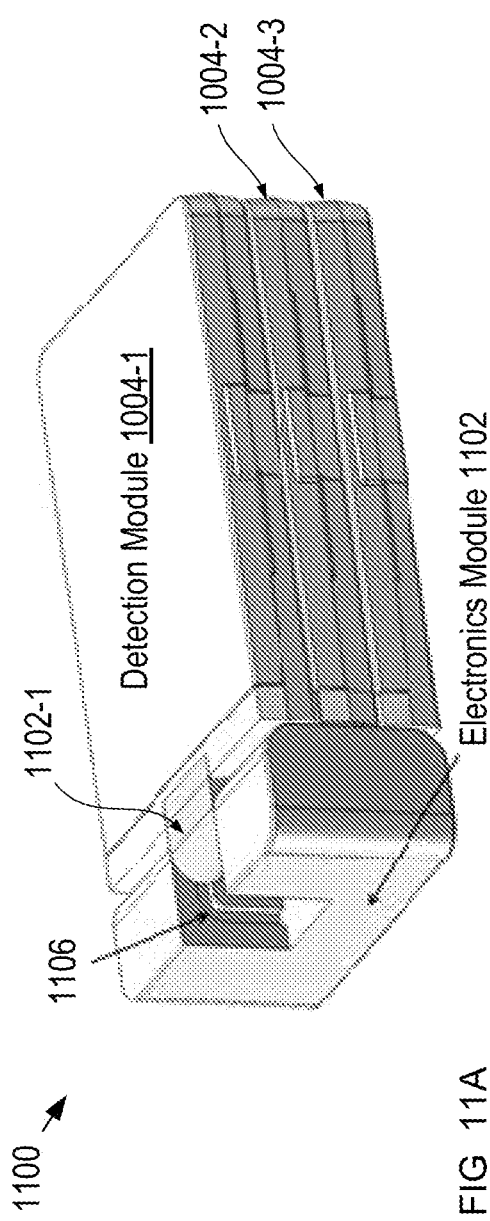
FIGS. 11A-B depicts schematic drawings of perspective views of another alternative example of a multi-prescription smart medicine case in its quiescent state and with one detection module rotated out, respectively, in accordance with the present disclosure.
Figure 11B:
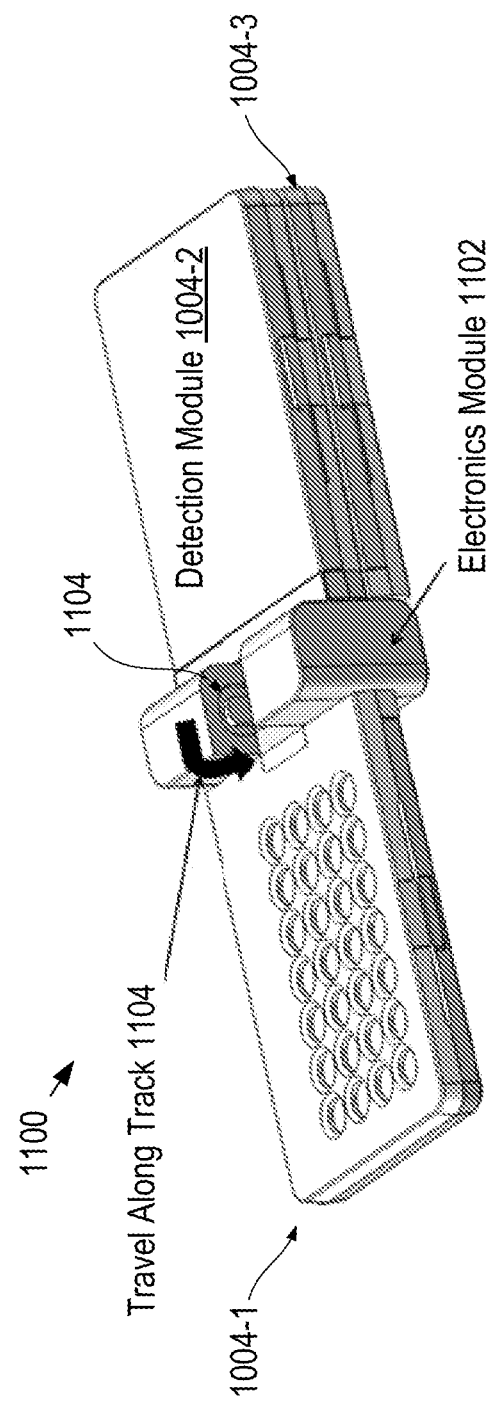

FIGS. 11A-B depicts schematic drawings of perspective views of another alternative example of a multi-prescription smart medicine case in its quiescent state and with one detection module rotated out, respectively, in accordance with the present disclosure. Case 1100 includes electronics module 1102, detection modules 1004-1 through 1004-3, and sliding connectors 1102-1 through 1102-3.

Electronics module 1102 is analogous to electronics module 102; however, electronics module 1102 includes translational track 1104, which enables each of detection modules 1004-1 through 1004-3 to slide out of the way of the detection modules underneath it.

Sliding connectors 1102-1 through 1102-3 are analogous to rotating connector 1006; however, each of sliding connectors 1102-1 through 1102-3 includes pins for engaging translational track 1104.

Translational track 1104 is an electrically conductive track that engages each of sliding connectors 1102-1 through 1102-3.

Translational track 1104 and sliding connectors 1102-1 through 1102-3 are configured such that each sliding connector can move along the translational track to enable access to an underlying detection module. In this example, accessing the detection modules is analogous to flipping the pages of a book. The electronics module is designed such that its internal components do not interfere with the translational track by, for example, locating them in the lower part of the module and/or in unused spaces on the sides of translational track.

Figure 12:
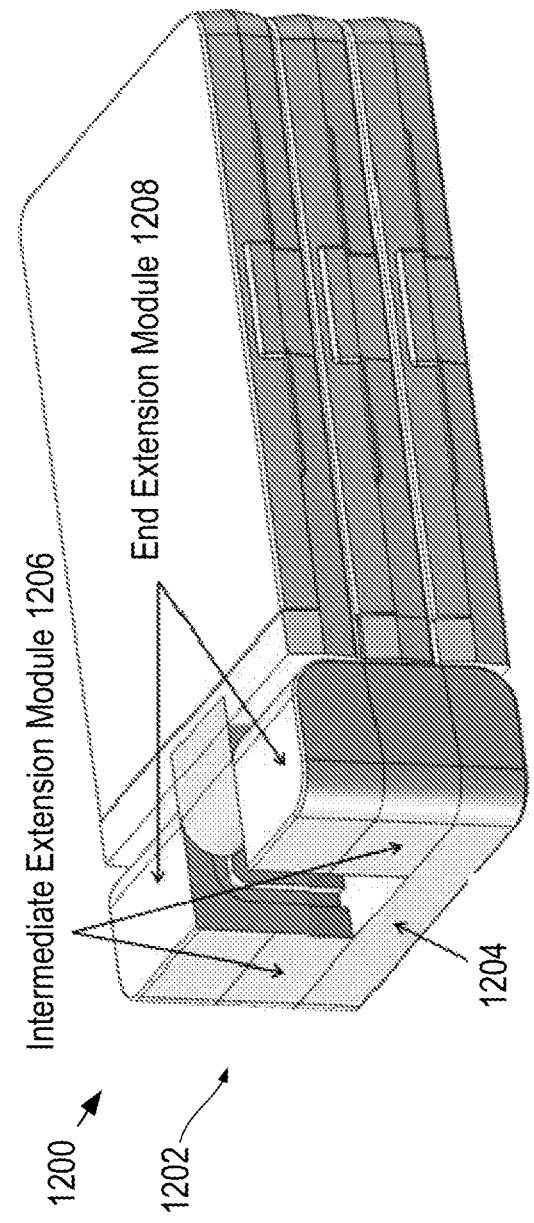
FIG. 12 depicts another alternative embodiment of a modular pill case in accordance with the present disclosure.

FIG. 12 depicts another alternative modular pill case in accordance with the present disclosure. Case 1200 is analogous to case 1100; however, in case 1200, the electronics module is expandable.

Specifically, electronics module 1202 includes base electronics module 1204, intermediate extension module 1206, and end extension module 1208.

Base electronics module 1204 forms a base for any practical number of intermediate extension modules 1206 and end extension module 1208.

Each extension module 1206 includes electrical routing and connectors that provide electrical connectivity between its corresponding detection module and the electronics module, as well as pass-through electrical connections that enable extension modules disposed on it to electrically connect with the electronics module.

End extension module 1208 is analogous to intermediate extension module 1206, but has electrical connectors only on its bottom surface, since it is designed to terminate the extension module stack. In addition, end extension module 1208 includes a u-shaped translation track on either side to terminate the composite translation track and enable the detection modules to flip over at the top of the extension module stack.

In some embodiments, an electrical bus is used to electrically connect extension and electronics modules, thereby reducing the amount of cabling and number of connectors per module. In such embodiments, each extension module includes the requisite electronics for identification and multiplexed operation.

For many users, pushing a tablet through the lidding film of a blister card can be difficult—particularly those suffering from arthritis and/or reduced strength. In addition, safety considerations can motivate making it difficult to push pills out of a blister card, such as for child-proof packaging.

Figure 13:
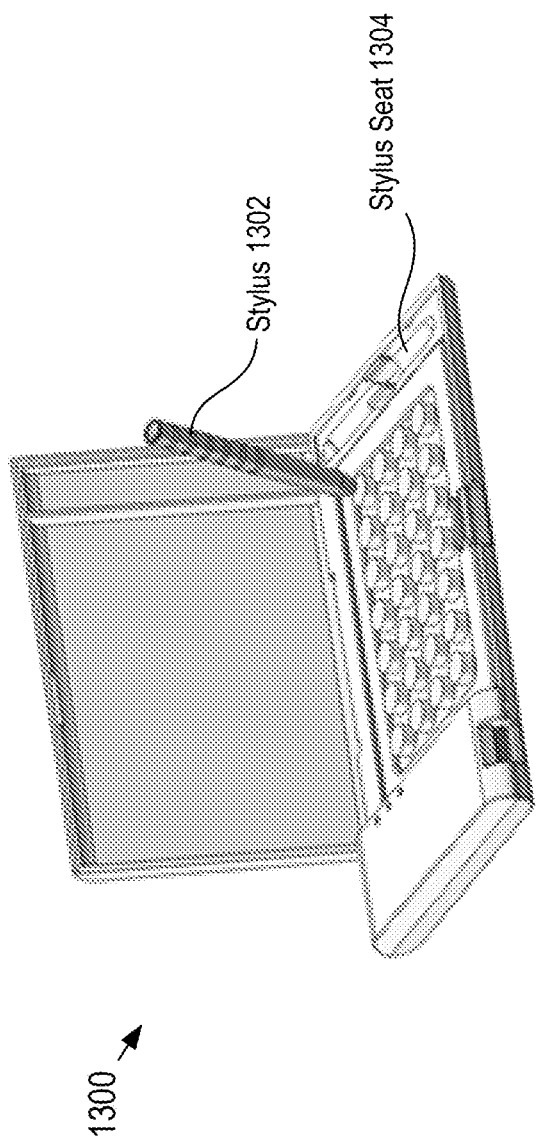
FIG. 13 depicts yet another alternative embodiment of a modular pill case in accordance with the present disclosure.

FIG. 13 depicts another alternative embodiment of a modular pill case in accordance with the present disclosure. Case 1300 includes stylus 1302 and stylus seat 1304.

Case 1300 is analogous to case 100; however, in case 1300 the detection module includes stylus seat 1304 for securing stylus 1302.

Stylus 1302 is a simple mechanical tool that is sufficiently rigid to enable it to exert enough pressure on a tablet to push it through the lidding film of its blister pack. Stylus 1302 has a tip whose shape is configured to enable it to remain on the blister during the act of dispensing a tablet. Typically, the tip shape is based on the size and shape of the pill and its blister. For example, in some applications, the stylus tip is rounded concavely with a contour that conforms to the shape of the tablet.

In some embodiments, stylus 1302 is augmented by the addition of sensing capability. Examples of smart stylus approaches in accordance with the present disclosure include, without limitation, inclusion of a sensor for sensing when a pill is pushed through the lidding film. A smart stylus in accordance with the present disclosure can include, without limitation:

i. a force sensor that detects a force that has been applied against the tip of the stylus; or
  ii. an electrical switch (e.g., ohmic, capacitive, etc.) positioned to close (or open) in response to a force exerted on the tip of the stylus; or
  iii. a photodiode (or camera) that measures the light intensity incident on the tip of the stylus, which would decrease when the tip is on a pill blister; or
  iv. a permanent magnet located at the tip of the stylus such that it induces a current in a planar coil patterned on the PCB underlying the blister card, where the coil is placed around the PCB's push-through hole of a pill; or
  v. a motion sensor (e.g., a 3-axis accelerometer) at or near the stylus' tip that detects a sudden deceleration impact that is indicative of the tip landing on a pill blister; or
  vi. any combination of i, ii, iii, iv, and v.

It should be noted that the output of a sensor disposed on stylus 1302 could be measured as a function of time to acquire a temporal profile of the applied force. This profile could then be compared to a reference profile indicative that a pill is (being) pushed through. In addition, the profile could be mined for additional user and pill dispensing insight. Elaborating the sensing in a smart stylus enables the collection of more and richer data.

For example, by tracking a motion sensor in stylus 1302, a user can be instructed to tap a reference location prior to landing the stylus on a pill blister. This reference location might, for example, be a point marked on the receiver under which the blister card is placed. The landing location of the stylus on the card, relative to the reference location, can then be estimated by integrating the output of the accelerometer twice in time. This data can be used to identify the location on the blister card from which the pill is dispensed. Since the integration time is very short, a consumer-grade accelerometer is typically sufficient for the required accuracy.

As another example, smart stylus that includes a camera chip at its tip can provide a measurement of the light intensity incident on the tip of the stylus. In addition, the camera chip could be used to provide images of a tablet and its immediate surrounding area, thereby providing additional data that facilitates identifying a pill and its location on the blister card. Identifying the pill location could be enabled by, for example, observing markings on the card itself, such as a printed pill number in the case of an OCP card.

In some embodiments, the stylus is battery-powered. In some embodiments, it is wirelessly powered. In some embodiments, it incorporates power-saving capabilities, such as a wake-up circuit. In some embodiments, it incorporates logic, memory, and wireless communication provisions. In some embodiments, it incorporates fingerprint sensing for user authentication.

The concepts described herein can be integrated into a medication adherence appliance. Such an appliance would be analogous, for example, to an 8-track music player, wherein, when an 8-track tape containing songs of an album is inserted into the player, the music on tracks becomes accessible to the listener. In this example, a detection module in accordance with the present disclosure is analogous to the tape, blisters on the card are analogous to the tracks, the pills are analogous to the music, and the electronics module is analogous to the player.

Similar to the 8-track player, in some embodiments, the insertion and ejection of a detection module is articulated with an electronically controlled mechanism incorporated into the appliance. In some embodiments, the stylus used to eject the pills is articulated with an electronically controlled mechanism, programmed to go to an intended blister site—either open loop or closed loop using detectable site markers—to push a pill through. The detection module might not have a lid since it is inserted into the appliance, further simplifying access by the autonomous stylus.

Such an appliance can be expanded to allow multiple detection modules, in much the same way that tape and compact disk players were developed to handle multiple tapes and compact disks, respectively. In similar fashion, such an appliance might be combined into a larger appliance (e.g., a car, computer, TV, etc.), furniture and built-ins (e.g., night stands, kitchen cabinets, etc.), or be placed on a countertop as a standalone unit.

A medication adherence appliance in accordance with the present disclosure can include a wide range of additional electronic and automation capabilities for added features and benefits. For example, electronics capabilities could include one or more displays for visualization, cameras for imaging, microphones for recording, speakers for audio, finger print sensor for user authentication, as well as radio, temperature sensors, humidity sensors, etc. Such capabilities would be applicable to single smart pill cases or multiple units of pill cases.

In many situations, medication is provided to the patient in a pill bottle. In these cases, the contents of the bottle would require transfer to a suitable blister-card equivalent in order to employ a smart medicine case in accordance with the present disclosure. The ability to accomplish such a transfer without additional tooling and supplies for blister card packaging would be advantageous.

Figure 14:
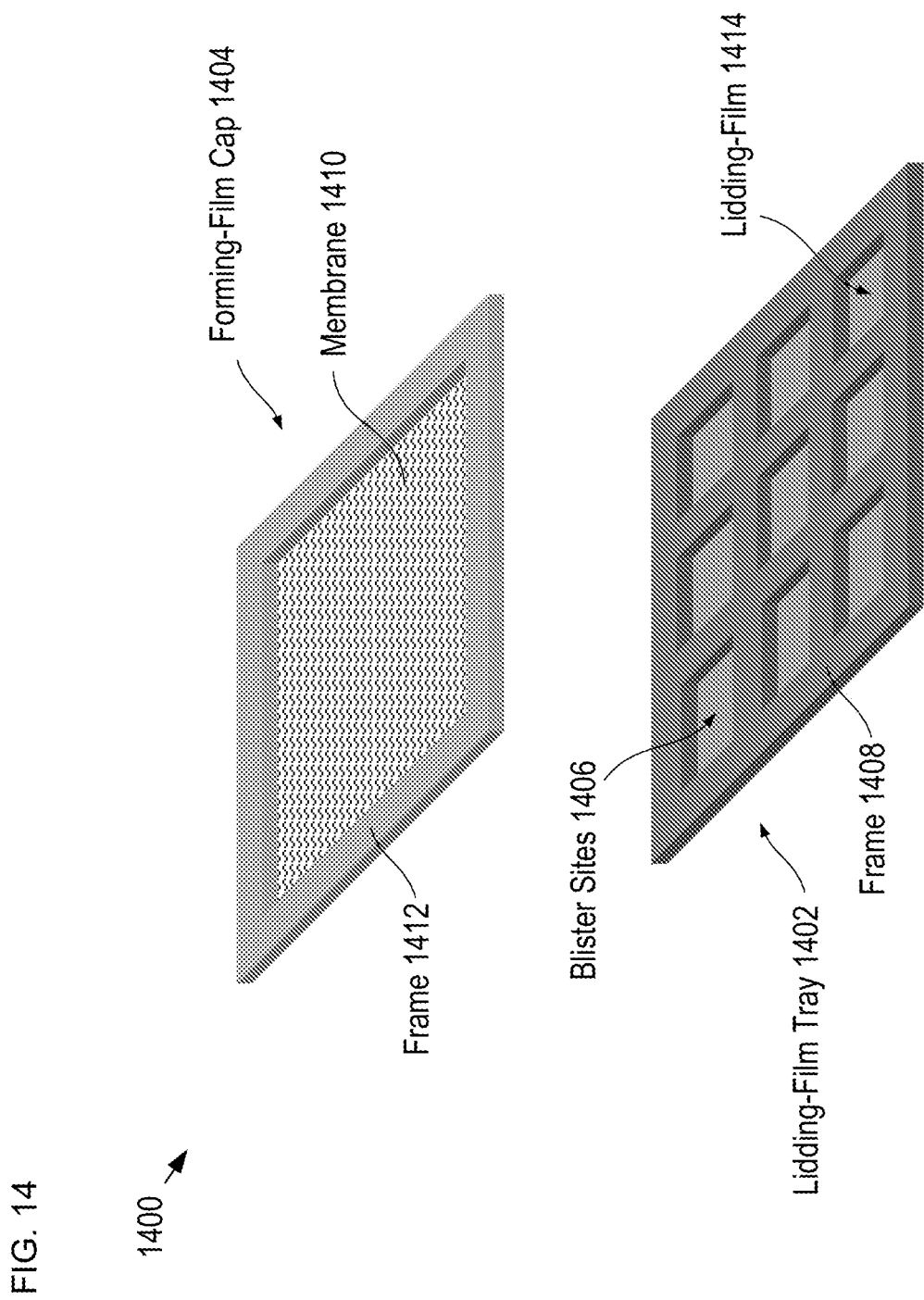
FIGS. 14 depicts an exploded perspective view of an exemplary pseudo-blister card in accordance with the present disclosure.

FIGS. 14 depicts an exploded perspective view of an exemplary pseudo-blister card in accordance with the present disclosure. Card 1400 comprises lidding-film tray 1402 and forming-film cap 1404.

Lidding-film tray 1402 includes a plurality of blister sites 1406, which comprise regions of lidding film 1414 located within open regions of substantially rigid frame 1408. Typically frame 1408 is made of a rigid plastic and lidding film 1414 is a thin sheet of a metal, such as aluminum; however, other materials can be used. Since it is broken at each blister site as its contents are dispensed, lidding-film tray 1402 is typically disposable and a new lidding-film tray would be needed once the pseudo-blister card is exhausted. In some embodiments, a lidding-film tray can be re-used simply by replacing lidding film 1414.

Forming-film cap 1404 includes forming-film membrane 1410, which is suspended from substantially rigid frame 1412.

To populate card 1400, a user places the intended tablets into each blister site 1406. Once all of the intended blister sites are populated with their proper tablets, the user places forming-film cap 1404 onto the lidding film tray. Typically, frame 1412 is designed to fit over the periphery of frame 1408. The populated pseudo-blister card can then be used with a compatible detection module or smart tablet case, as described above vis-à-vis commercially provided blister cards.

Card 1400 is configured to fit any practical desired number, shape, and size of blister sites. In the depicted example, card 1400 includes nine rectilinear blister sites 1406, each intended to hold a single tablet; however, any practical shape and/or number of blister sites can be used. Examples of suitable blister-site shapes include, without limitation, circular, elliptical, hexagonal, etc. The number of blister sites and their arrangement is typically determined based on a variety of considerations, including the medication refill cycle, frequency of replenishment by the caregiver, and the like. For example, OCP blister cards are available in weekly prescriptions having a 1×7 arrangement blister-site format, 28-day OCP cards having a 4×7 arrangement format, among others.

Furthermore, in some embodiments, at least one blister site 1406 contains more than one tablet, such as when a higher dose of one medication is required and/or to facilitate a combination dose of different medications. In some embodiments, blister sites 1406 on a single pseudo-blister card are non-uniform to enable it to contain a mix of different tablet sizes and shapes.

Preferably, the portion of lidding-film 1414 functioning as the bottom of each blister site is contoured during manufacture so that tablets will slide toward the centers of their respective site. For example, in some embodiments, the lidding film is provided a convex (i.e., elevated) surface around the periphery of the site and a concave (depressed) surface near the center of the site. In some embodiments, one or more of the blister sites are not contoured.

In some embodiments, lidding film tray 1404 is used in a "flipped-over" configuration, in which the lidding film is contoured and has a concave surface right from the site's periphery.

In some embodiments, forming-film cap 1404 is made reusable by employing an elastic material for membrane 1410. As a result, the membrane can recover its original shape after the content of a blister site content is dispensed. Materials suitable for use in reusable membrane 1410 include, without limitation, rubber-like polymers, elastomers, and the like.

In some embodiments, markings (e.g., text, signs, colors, etc.) are printed on forming-film cap 1404 to support the user's adherence and/or indicate medication information. Examples of such markings include, without limitation, numbers for days, medication name, dosing information, etc. In some embodiments, such information is provided in the form of stickers that can be adhered to the forming-film cap.

Figure 15:
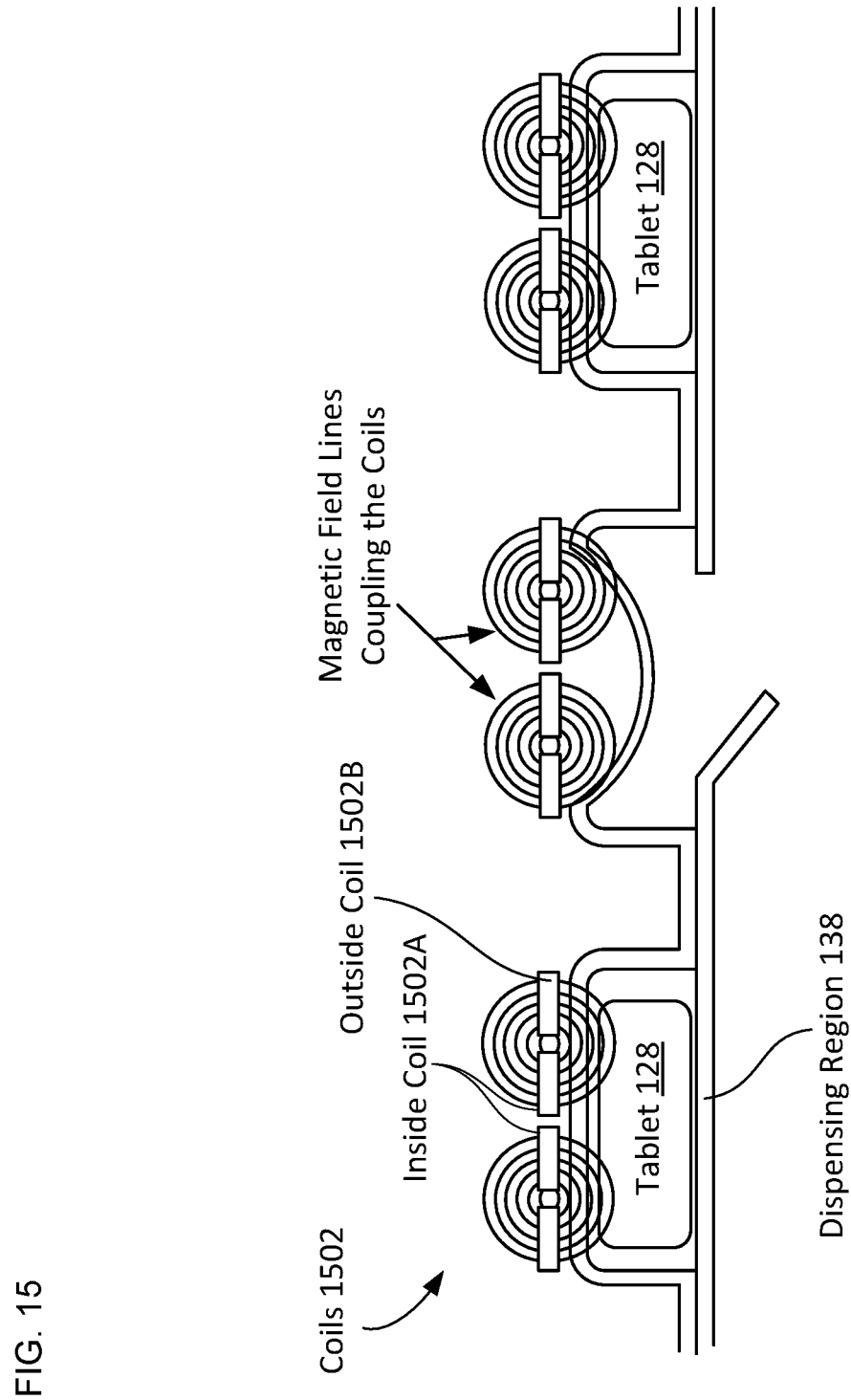
FIG. 15 depicts a cross-sectional drawing of a portion of an alternative detection system suitable for use in detection module 104.

FIG. 15 depicts a cross-sectional drawing of a portion of an alternative detection system suitable for use in detection module 104. Detection module 1500 includes planar coils 1502, which are arranged on a substrate (not shown) in an arrangement that matches that of the tablets of blister card 126.

Planar coils 1502 are concentric coils of electrically conductive material that is disposed on a substrate. Planar coils 1502 include inside coil 1502A and outside coil 1502B. Typically, the substrate is located on the underside of lid 318. When lid 318 is closed, each coil pair is moved into proximity with a different one of reservoirs 136. Since the permeability of an empty reservoir is different than that of a reservoir that contains a tablet 128, a difference in the magnetic flux density coupling the coils can be readily detected in each case. The detected difference indicates the content state of a reservoir. Pushing a current through one coil and measuring the induced current in the other enables measurement of the mutual inductance of a coil pair.

It is to be understood that the disclosure teaches just exemplary embodiments and that many variations can easily be devised by those skilled in the art after reading this disclosure and that the scope of the present invention is to be determined by the following claims.

What is claimed is:

1. A modular case for monitoring the state of a first blister card that includes a first forming film, a first lidding film, and a first tablet contained in a first reservoir defined by the first forming film and the first lidding film, wherein the modular case comprises:
  (1) a first detection module comprising:
    (i) a first housing for holding the first blister card;
    (ii) a first receiver that includes a seat and a frame that is movable relative to the seat; and
    (iii) a first sensor that is operative for providing a first electrical signal that is based on at least one of (a) the presence of the first tablet in the first reservoir and (b) the physical state of a first dispensing region of the first lidding film;
    wherein the seat and frame are collectively configured to reversibly locate the first blister card in a first position in which the blister card and first sensor are operatively coupled;
  (2) a first electronics module comprising:
    (i) first sensor circuitry that is operative for measuring the first electrical signal;
    (ii) first communications circuitry configured to communicate with an external device; and
    (iii) a second housing for enclosing the first sensor circuitry and the first communications circuitry; and
  (3) a first electrical interface that is configured to reversibly electrically couple the first sensor and the first sensor circuitry, wherein the first electrical interface includes a first socket and a first plug, and wherein the first electronics module comprises one of the first plug and the first socket, and wherein the first detection module comprises the other one of the first plug and the first socket.

2. The modular case of claim 1 further comprising (4) a first mechanical interface that is configured to physically align and reversibly mechanically couple the first housing and the second housing and physically align the first electronics module and the first detection module and physically align the first socket and first plug.

3. The modular case of claim 1 further comprising (4) a first latch that is configured to reversibly lock the first electronics module and first detection module together.

4. The modular case of claim 1 wherein the first electronics module further includes (iv) sleep-mode circuitry that is operative for putting the first electronics module into a low-power-dissipation mode and activate the first electronics module in response to an environmental stimulus such that the first electronics module exits the low-power-dissipation mode.

5. The modular case of claim 1 wherein the first sensor is a capacitance sensor configured to provide the first signal based on a first capacitance whose magnitude is based on the state of the first dispensing region.

6. The modular case of claim 5 wherein the first sensor includes:
  a first electrode that lies in a first plane that is substantially parallel with the first dispensing region when the blister card is in the first position.

7. The modular case of claim 6 wherein the first electrode includes a first portion and a second portion that define a first capacitor having the first capacitance, and wherein the first capacitance is based on a fringing field between the dispensing region and the first electrode.

8. The modular case of claim 6 wherein the first sensor further includes a second electrode that lies in a second plane that is substantially parallel with the first plane, wherein the second plane is between the first plane and the lidding film when the blister card is in the first position.

9. The modular case of claim 8 wherein the first electrode is configured to function as an electrical shield for the second electrode.

10. The modular case of claim 9 wherein the second electrode includes a first portion and a second portion that define a first capacitor having the first capacitance, and wherein the first capacitance is based on a fringing field between the dispensing region and the first electrode.

11. The modular case of claim 6 wherein the first sensor further includes a second electrode and a third electrode, and wherein the second electrode lies in a second plane that is between the first plane and the lidding film when the blister card is in the first position, and wherein the third electrode lies in a third plane, the first plane being between the second plane and the third plane, and further wherein the second electrode and the third electrode collectively define an electrical shield for the first electrode.

12. The modular case of claim 1 further comprising:
 (4) a second detection module, the second detection module comprising:
  (i) a third housing for holding a second blister card;
  (ii) a second receiver that is configured to locate the second blister card in a second position within the second housing; and
  (iii) a second sensor that is configured to operatively couple with the second blister card when the second blister card is in the second position such that the second sensor is operative for providing a second electrical signal that is based on at least one of (a) the presence of the second tablet in the second reservoir and (b) the physical state of a second dispensing region of the second lidding film; and
 (5) a second electrical interface that is configured to reversibly electrically couple the second sensor and the first sensor circuitry, wherein the second electrical interface includes a second socket and a second plug, and wherein the first electronics module comprises one of the second plug and the second socket, and wherein the second detection module comprises the other one of the second plug and the second socket;
 wherein the first sensor circuitry is further operative for measuring the second electrical signal.

13. The modular case of claim 1 further comprising:
 (4) a second detection module, the second detection module comprising:
  (i) a third housing for holding a second blister card;
  (ii) a second receiver that is configured to locate the second blister card in a second position within the third housing; and
  (iii) a second sensor that is configured to operatively couple with the second blister card when the second blister card is in the second position such that the second sensor is operative for providing a second electrical signal that is based on at least one of (a) the presence of the second tablet in the second reservoir and (b) the physical state of a second dispensing region of the second lidding film;
 (5) a second electronics module comprising:
  (i) second sensor circuitry that is operative for measuring the second electrical signal;
  (ii) second communications circuitry configured to communicate with the external device; and
  (iii) a fourth housing for enclosing the second sensor circuitry and the second communications circuitry; and
 (6) a second electrical interface that is configured to reversibly electrically couple the second sensor and the second sensor circuitry, wherein the second electrical interface includes a second socket and a second plug, and wherein the second electronics module comprises one of the second plug and the second socket, and wherein the second detection module comprises the other one of the second plug and the second socket;
 wherein the first electrical module and the second electrical module are physically coupled.

14. The modular case of claim 1 further comprising (4) a stylus, wherein the stylus includes a second sensor that is selected from the group consisting of a force sensor, an electrical switch that is actuated by a force exerted between the stylus and the first reservoir, a photodiode, a magnetic sensor, and a motion sensor.

15. The modular case of claim 1 wherein the first sensor includes a first plurality of electrodes that arranged around the periphery of the first lidding film and electrically coupled with the first lidding film when the first blister card is located in the first receiver.

16. The modular case of claim 15 wherein the first plurality of electrodes is arranged to enable a four-point-probe measurement of at least a portion of the first lidding film.

17. The modular case of claim 1 wherein the first sensor is selected from the group consisting of a strain sensor, an optical sensor, an acoustic sensor, and a tactile sensor.

18. The modular case of claim 1 wherein the first housing includes a body and a lid that is movable relative to the body, the lid having an open position and a closed position, and wherein the first sensor includes a magnetic sensor having a first planar coil and a second planar coil, the first and second planar coils being concentric and disposed on the lid such that the magnetic sensor is configured to detect the permeability of the first reservoir when the lid is in the closed position.

19. The modular case of claim 1 wherein the first detection module includes at least one indicator that enables at least one of (i) identification of the brand of the first blister card and (ii) detection that the first blister card is counterfeit.

20. A method for monitoring the state of at least one blister card, wherein the method comprises:
 (1) providing a first detection module comprising:
  (i) a first housing for holding a first blister card, wherein the first blister card includes a first forming film, a first lidding film, and a first plurality of tablets, each tablet of the first plurality thereof being held within a different first reservoir of a plurality thereof, the plurality of first reservoirs being arranged in a first arrangement, and each first reservoir of the plurality thereof including a first dispensing region;
  (ii) a first receiver that includes a seat and a frame that is movable relative to the seat; and
  (iii) a first plurality of sensors that is arranged in the first arrangement, the first plurality of sensors being operative for providing a first plurality of electrical signals, each electrical signal of the first plurality thereof being based on at least one of (a) the presence of a different tablet of the first plurality thereof and (b) the state of a different first dispensing region of the plurality thereof;

wherein the seat and frame are collectively configured to reversibly locate the first blister card within the first housing such that the first blister card and first plurality of sensors are operatively coupled; and (2) reversibly electrically coupling the first detection module and a first electronics module at a first electrical interface comprising a first socket and a first plug, wherein the first electronics module includes:
   (i) first sensor circuitry that is operative for measuring each electrical signal of the first plurality thereof;
   (ii) first communications circuitry configured to communicate with an external device; and
   (iii) a second housing for enclosing the first sensor circuitry and the first communications circuitry;

wherein the first electronics module comprises one of the first plug and the first socket, and wherein the first detection module comprises the other one of the first plug and the first socket.

21. The method of claim 20 further comprising:
(3) locating the first blister card in the first detection module;
(4) determining a physical state of the first blister card based on the first plurality of electrical signals; and
(5) comparing the physical state of the first blister card with an expected state of the first blister card, wherein the expected state is based on a predetermined prescription regimen for the first plurality of tablets; and
(6) providing a first output signal based on the physical state of the first blister card relative to the expected state.

22. The method of claim 20 further comprising verifying the compatibility of the first blister card and the first detection module by operations comprising:
(3) determining the number of sensors in the first detection module;
(4) providing the identity of the first blister card to the external device, wherein the identity denotes the number of tablets in the first blister card;
(5) making a first comparison between the number of sensors in the first detection module and the number of tablets in the first blister card; and
(6) issuing a first status signal based on the first comparison.

23. The method of claim 20 further comprising:
reversibly physically coupling the first detection module and the first electronics module via a mechanical interface having a first portion that is included in one of the first detection module and the first electronics module and a second portion included in the other one of the first detection module and the first electronics module, wherein the first and second portions are configured to enable only one orientation between the first detection module and the first electronics module when they are physically coupled.

24. The method of claim 20 wherein the first detection module is provided such each of the plurality of sensors is a capacitance sensor configured to provide a different electrical signal of the first plurality thereof based on a first capacitance whose magnitude is based on the state of its respective first dispensing region.

25. The method of claim 24 wherein each of the plurality of sensors includes:

a first electrode that lies in a first plane that is substantially parallel with a different dispensing region of the plurality thereof when the blister card is in the first position.

26. The method of claim 25 wherein the first electrode includes a first portion and a second portion that define a first capacitor having the first capacitance, and wherein the first capacitance is based on a fringing field between the dispensing region and the first electrode.

27. The method of claim 25 wherein each sensor of the plurality thereof further includes a second electrode that lies in a second plane that is substantially parallel with the first plane, wherein the second plane is between the first plane and the lidding film when the blister card is in the first position.

28. The method of claim 25 wherein the first sensor further includes a second electrode and a third electrode, and wherein the second electrode lies in a second plane that is between the first plane and the lidding film when the blister card is in the first position, and wherein the third electrode lies in a third plane, the first plane being between the second plane and the third plane, and further wherein the second electrode and the third electrode collectively define an electrical shield for the first electrode.

29. The method of claim 20 further comprising:
(3) providing a second detection module, the second detection module comprising:
   (i) a third housing for holding a second blister card, wherein the second blister card includes a second forming film, a second lidding film, and a second plurality of tablets, each tablet of the second plurality thereof being held within a different second reservoir of a plurality thereof, the plurality of second reservoirs being arranged in a second arrangement, and each second reservoir of the plurality thereof including a second dispensing region;
   (ii) a second receiver that is configured to locate the second blister card in a second position within the third housing; and
   (iii) a second plurality of sensors that is arranged in the second arrangement, the second plurality of sensors being operative for providing a second plurality of electrical signals, each electrical signal of the second plurality thereof being based on at least one of (a) the presence of a different tablet of the second plurality thereof and (b) the state of a different second dispensing region of the plurality thereof; and
(4) reversibly electrically coupling the second detection module and the first electronics module at a second electrical interface comprising a second socket and a second plug, wherein the first electronics module comprises one of the second plug and the second socket, and wherein the second detection module comprises the other one of the second plug and the second socket;

wherein the first sensor circuitry is further operative for measuring the second electrical signal.

30. The method of claim 20 further comprising:
(3) providing a second detection module, the second detection module comprising:
   (i) a third housing for holding a second blister card, wherein the second blister card includes a second forming film, a second lidding film, and a second plurality of tablets, each tablet of the second plurality thereof being held within a different second reservoir of a plurality thereof, the plurality of second reservoirs being arranged in a second arrangement, and each second reservoir of the plurality thereof including a second dispensing region;

(ii) a second receiver that is configured to locate the second blister card in a second position within the third housing; and (iii) a second plurality of sensors that is arranged in the second arrangement, the second plurality of sensors being operative for providing a second plurality of electrical signals, each electrical signal of the second plurality thereof being based on at least one of (a) the presence of a different tablet of the second plurality thereof and (b) the state of a different second dispensing region of the plurality thereof; and (4) reversibly electrically coupling the second detection module and a second electronics module at a second electrical interface comprising a second socket and a second plug, wherein the first electronics module comprises one of the second plug and the second socket, and wherein the second detection module comprises the other one of the second plug and the second socket, and wherein the second electronics module comprises:

(i) second sensor circuitry that is operative for measuring each electrical signal of the second plurality thereof;

(ii) second communications circuitry configured to communicate with the external device; and (iii) a fourth housing for enclosing the second sensor circuitry and the second communications circuitry; and (5) a second electrical interface that is configured to reversibly electrically couple the second sensor and the second sensor circuitry, wherein the second electrical interface includes a second socket and a second plug, and wherein the second electronics module comprises one of the second plug and the second socket, and wherein the second detection module comprises the other one of the second plug and the second socket.

31. The method of claim 21 wherein the first output signal includes an alert that indicates a refill of the blister card is due.

32. The method of claim 27 wherein the first electrode is configured to function as an electrical shield for the second electrode.

33. The method of claim 32 wherein the second electrode includes a first portion and a second portion that define a first capacitor having the first capacitance, and wherein the first capacitance is based on a fringing field between the dispensing region and the first electrode.

* * * * *